US011903945B2

(12) United States Patent
Lee et al.

(10) Patent No.: US 11,903,945 B2
(45) Date of Patent: Feb. 20, 2024

(54) METHODS OF TREATING ANTIPSYCHOTIC-INDUCED WEIGHT GAIN WITH MIRICORILANT

(71) Applicant: Corcept Therapeutics Incorporated, Menlo Park, CA (US)

(72) Inventors: Ada Lee, Menlo Park, CA (US); Joseph Belanoff, Menlo Park, CA (US); Hazel Hunt, West Sussex (GB)

(73) Assignee: Corcept Therapeutics Incorporated, Menlo Park, CA (US)

( * ) Notice: Subject to any disclaimer, the term of this patent is extended or adjusted under 35 U.S.C. 154(b) by 339 days.

(21) Appl. No.: 17/119,582

(22) Filed: Dec. 11, 2020

(65) Prior Publication Data

US 2021/0177848 A1 Jun. 17, 2021

Related U.S. Application Data

(60) Provisional application No. 62/946,957, filed on Dec. 11, 2019.

(51) Int. Cl.
*A61K 31/513* (2006.01)
*A61K 31/551* (2006.01)
*A61P 3/04* (2006.01)

(52) U.S. Cl.
CPC .............. *A61K 31/513* (2013.01); *A61P 3/04* (2018.01)

(58) Field of Classification Search
CPC ........ A61K 31/513; A61K 31/551; A61P 3/04
See application file for complete search history.

(56) References Cited

U.S. PATENT DOCUMENTS

| | | | |
|---|---|---|---|
| 4,963,558 | A | 10/1990 | Hotten et al. |
| 5,929,058 | A | 7/1999 | Deisher |
| 6,150,349 | A | 11/2000 | Schatzberg et al. |
| 6,369,046 | B1 | 4/2002 | Schatzberg et al. |
| 6,680,310 | B2 | 1/2004 | Belanoff et al. |
| 6,852,719 | B2 | 2/2005 | Liu et al. |
| 7,576,076 | B2 | 8/2009 | Clark et al. |
| 7,678,813 | B2 | 3/2010 | Clark et al. |
| 7,790,745 | B2 | 9/2010 | Yang et al. |
| 7,799,782 | B2 | 9/2010 | Munson et al. |
| 7,928,237 | B2 | 4/2011 | Clark et al. |
| 8,173,664 | B2 | 5/2012 | Clark et al. |
| 8,324,203 | B2 | 12/2012 | Clark et al. |
| 8,461,172 | B2 | 6/2013 | Clark et al. |
| 8,557,839 | B2 | 10/2013 | Clark et al. |
| 8,598,154 | B2 | 12/2013 | Clark et al. |
| 8,685,973 | B2 | 4/2014 | Clark et al. |
| 8,859,774 | B2 | 10/2014 | Hunt et al. |
| 8,889,867 | B2 | 11/2014 | Clark et al. |
| 8,906,917 | B2 | 12/2014 | Clark et al. |
| 8,969,557 | B2 | 3/2015 | Harriman et al. |
| 9,273,047 | B2 | 3/2016 | Hunt et al. |
| 9,422,323 | B2 | 8/2016 | Houpis et al. |
| 9,707,223 | B2 | 7/2017 | Hunt et al. |
| 9,943,505 | B2 | 4/2018 | Hunt et al. |
| 9,956,216 | B2 | 5/2018 | Hunt et al. |
| 10,047,082 | B2 | 8/2018 | Hunt et al. |
| 10,117,852 | B2 | 11/2018 | Hunt et al. |
| 10,213,414 | B2 | 2/2019 | Hunt et al. |
| 10,323,034 | B2 | 6/2019 | Hunt et al. |
| 10,787,449 | B2 | 9/2020 | Hunt et al. |
| 2006/0128688 | A1 | 6/2006 | Tonnaer |
| 2006/0223852 | A1 | 10/2006 | Gillespie et al. |
| 2007/0281928 | A1 | 12/2007 | Clark et al. |
| 2008/0070950 | A1 | 3/2008 | Benjamin et al. |

(Continued)

FOREIGN PATENT DOCUMENTS

| | | |
|---|---|---|
| CL | 2013002667 A1 | 5/2014 |
| CN | 1965840 A | 5/2007 |

(Continued)

OTHER PUBLICATIONS

ClinicalTrials, 2019, https://clinicaltrials.gov/ct2/show/NCT03877562.*
CorceptTherapeutics, 2019, https://seekingalpha.com/article/4304715-corcept-therapeutics-cort-ceo-joseph-belanoff-on-q3-2019-results-earnings-call-transcript.*
"Corcept Therapeutics Announces Third Quarter 2019 Financial Results and Provides Corporate Update", Metabolic Disease, Available online at: https://www.sec.gov/Archives/edgar/data/1088856/000162828019013657/exhibit991pressrelease.htm, Nov. 7, 2019, 7 pages.
Belanoff et al., "Selective Glucocorticoid Receptor (Type II) Antagonist Prevents and Reverses Olanzapine-induced Weight Gain", Diabetes, Obesity and Metabolism, vol. 12, 2010, pp. 545-547.

(Continued)

*Primary Examiner* — Sun Jae Yoo
(74) *Attorney, Agent, or Firm* — Kilpatrick Townsend & Stockton LLP

(57) ABSTRACT

Methods of Treating Antipsychotic-Induced Weight Gain with Miricorilant Methods and compositions for treating a subject at risk of, or suffering from antipsychotic-induced weight gain are disclosed. The methods include administration of a cyclohexyl pyrimidine glucocorticoid receptor modulator (GRM) such as miricorilant (CORT118335) to a patient receiving, or who has received, or who is expected to receive, an antipsychotic drug such as olanzapine, risperidone, clozapine, or other weight-inducing antipsychotic medication. The GRM (e.g., miricorilant) may be orally administered. Administration of such a GRM along with antipsychotic medication may reduce the amount of weight, or reduce the rate of weight gain, or prevent weight gain, otherwise due to antipsychotic medication alone. The methods may reverse weight gain in a patient previously administered antipsychotic medication. Administration of such a GRM with antipsychotic medication may reduce, or reduce gain in, or prevent gain in, or reverse gain in, insulin resistance or blood levels of liver enzymes (AST, ALT), triglycerides, or insulin.

18 Claims, 3 Drawing Sheets

(56) References Cited

U.S. PATENT DOCUMENTS

| | | |
|---|---|---|
| 2010/0179115 A1 | 7/2010 | Belanoff |
| 2010/0292477 A1 | 11/2010 | Clark et al. |
| 2010/0311717 A1 | 12/2010 | McIntosh et al. |
| 2011/0166110 A1 | 7/2011 | Clark et al. |
| 2012/0220565 A1 | 8/2012 | Clark et al. |
| 2013/0072486 A1 | 3/2013 | Clark et al. |
| 2013/0225633 A1 | 8/2013 | Hunt et al. |
| 2014/0315866 A1 | 10/2014 | Pan et al. |
| 2015/0148341 A1 | 5/2015 | Hunt et al. |

FOREIGN PATENT DOCUMENTS

| | | |
|---|---|---|
| EP | 0037495 A1 | 10/1981 |
| EP | 0145121 A2 | 6/1985 |
| EP | 0369627 A2 | 5/1990 |
| EP | 0375210 A1 | 6/1990 |
| EP | 0375210 B1 | 5/1995 |
| EP | 0722732 A1 | 7/1996 |
| EP | 1778236 A1 | 5/2007 |
| EP | 1778236 | 7/2010 |
| EP | 3074011 B1 | 7/2019 |
| JP | 322220 B | 4/1957 |
| JP | 4368384 A | 12/1992 |
| JP | 6128238 A | 5/1994 |
| JP | 9505030 A | 5/1997 |
| JP | 1017555 A | 1/1998 |
| JP | 2002506032 A | 2/2002 |
| JP | 2002544271 A | 12/2002 |
| WO | 9410150 A1 | 5/1994 |
| WO | 9504734 A1 | 2/1995 |
| WO | 9945925 A1 | 9/1999 |
| WO | 0069846 A1 | 11/2000 |
| WO | 0244120 A1 | 6/2002 |
| WO | 03009853 A1 | 2/2003 |
| WO | 03015692 A2 | 2/2003 |
| WO | 03061651 A1 | 7/2003 |
| WO | 03084935 A2 | 10/2003 |
| WO | 2004065351 A1 | 8/2004 |
| WO | 2005087769 A1 | 9/2005 |
| WO | 2009058944 A2 | 5/2009 |
| WO | 2010132445 A1 | 11/2010 |
| WO | 2012027702 A1 | 3/2012 |
| WO | 2012094618 A1 | 7/2012 |
| WO | 2013177559 A2 | 11/2013 |

OTHER PUBLICATIONS

Application No. PCT/US2020/064520, International Search Report and Written Opinion, dated Apr. 8, 2021, 13 pages.

International Patent Application No. PCT/US2020/064520, "International Preliminary Report on Patentability", dated Jun. 23, 2022, 7 pages.

Allison et al., Antipsychotic-Induced Weight Gain: A Comprehensive Research Synthesis, American Journal of Psychiatry, vol. 156, No. 11, Nov. 11, 1999, pp. 1686-1696.

Amorphous Solid, Wikepedia, Available Online at: http://en.wikipedia.org/wiki/Amorphous_solid, Jan. 16, 2014, 3 pages.

Andrews et al., Glucocorticoids and Insulin Resistance: Old Hormones, New Targets, Clinical Science, vol. 96, No. 5, Jun. 1999, pp. 513-523.

Antipsychotic Drugs: The Weight Problem, Harvard Mental Health Letter, Harvard Health Online, Dec. 2000, 4 pages.

Baptista et al., Body Weight Gain After Administration of Antipsychotic Drugs: Correlation with Leptin, Insulin and Reproductive Hormones, Pharmacopsychiatry, vol. 33, No. 3, May 2000, pp. 81-88.

Baptista, Body Weight Gain Induced by Antipsychotic Drugs: Mechanisms and Management, Acta Psychiatrica Scandinavica, vol. 100, No. 1, Jul. 1999, pp. 3-16.

Barth et al., Structural and Stereoelectronic Requirements for the Inhibition of Mammalian 2,3-Oxidosqualene Cyclase by Substituted Isoquinoline Derivatives, Journal of Medicinal Chemistry, vol. 39, No. 12, American Chemical Society, Jun. 7, 1996, pp. 2302-2312.

Bhuyan et al., Studies on Uracils: Synthesis of Novel Uracil Analogues via 1,5- and 1,6-Intramolecular Cycloaddition Reactions, Journal of Chemical Research, Synopses, vol. 9, 1998, pp. 502-503.

Blackburn, Weight Gain and Antipsychotic Medication, The Journal of Clinical Psychiatry, vol. 61, No. 8, 2000, pp. 36-42.

Bledsoe et al., Crystal Structure of the Glucocorticoid Receptor Ligand Binding Domain Reveals a Novel Mode of Receptor Dimerization and Coactivator Recognition, Cell, vol. 110, No. 1, Jul. 12, 2002, pp. 93-105.

Christoffers et al., Absolute Configuration of Methyl (+)-1,2,3,4,6,7,8,8a-Octahydro-6-isoquinolone-8a-carboxylate and Stereochemistry of a Copper-Catalyzed Asymmetric Michael Reaction, Zeitschrift Fuer Naturforschung B Chemical Sciences, vol. 59, No. 4, Apr. 1, 2004, pp. 375-379.

Christoffers et al., Copper-Catalyzed Asymmetric Michael Reactions with a-Amino Acid Amides: Synthesis of an Optically Active Piperidine Derivative, Wiley Online Library, vol. 2002, No. 9, May 2002, pp. 1505-1508.

Christoffers et al., Synthesis of an Optically Active Decahydro-6-Isoquinolone Scaffold with a Quaternary Stereocenter, Wiley Online Library, vol. 2004, No. 12, Jun. 2004, pp. 2701-2706.

Christoffers, Transformation of an Optically Active Decahydro-6-isoquinolone Scaffold: Perfect Felkin-Anh Diastereoselectivity, Organic Letters, vol. 6, No. 7, American Chemical Society, Feb. 3, 2004, pp. 1171-1173.

Chu et al., Successful Long-Term Treatment of Refractory Cushing's Disease with High-Dose Mifepristone (RU 486), The Journal of Clinical Endocrinology & Metabolism, vol. 86, No. 8, Aug. 1, 2001, pp. 3568-3573.

Chu, Connecting Via Winsock to SIN at PTO-STN on Port 23, STN-12691012, STN International, Mar. 19, 2012, 62 pages.

Clark et al., 1H-Pyrazolo[3,4-g]Hexahydro-Isoquinolines as Selective Glucocorticoid Receptor Antagonists with High Functional Activity, Bioorganic & Medicinal Chemistry Letters, vol. 18, No. 4, Feb. 15, 2008, pp. 1312-1317.

Database Crossfile Beilstein, Beilstein Institut Zur Foerderung der Chemischen Wissenschaft, Accession No. 101172-52-5 (BRN), Jun. 27, 1988, 3 pages.

Dibas et al., Glucocorticoid Therapy and Ocular Hypertension, European Journal of Pharmacology, vol. 787, Sep. 15, 2016, pp. 1-33.

Dorwald, Side Reactions in Organic Synthesis, Wiley: VCH, Weinheim. Preface and Chapter 1, 2005, 18 pages.

Elmore, Nonsteroidal Selective Glucocorticoid Modulatores: The Effect of C-5 Alkyl Substitution on the Transcriptional Activation/Repression Profile of 2,5-Dihydro-10-Methoxy-2,2,4-Trimethyl-1H-[1] Benzopyrano[3,4-f]Quinolines, American Chemical Society, Journal of Medicinal Chemistry, vol. 44, No. 25, Dec. 1, 2001, pp. 4481-4491.

Friedman et al., Phosphoenolpyruvate Carboxykinase (GTP) Gene Transcription and Hyperglycemia Are Regulated by Glucocorticoids in Genetically Obese db/db Transgenic Mice, Journal of Biological Chemistry, vol. 272, No. 50, Dec. 12, 1997, pp. 31475-31481.

Fukazawa et al., 6-Amino-5-Methyluracil Derivatives and Their Use as Thymidine Phosphorylase Inhibitors and Neovascularization Inhibitors, XP002355358; Database CA Online; Chemical Abstracts Service; Database Accession No. 1998:59356, Abstract, 1998, 4 pages.

Gasparini et al., Peripheral Markers in Testing Pathophysiological Hypotheses and Diagnosis Alzheimer's Disease, Federation of American Societies for Experimental Biology Journal, vol. 12, 1998, pp. 17-34.

Gauthier et al., Alzheimer's Disease: Current Knowledge, Management and Research, Canadian Medical Association Journal, vol. 157, No. 8, Oct. 15, 1997, pp. 1047-1052.

Genck, A Number of Factors Can Affect Solids Formation, Available Online at https://www.chemicalprocessing.com/articles/2010/210/?page=print, 2004, pp. 1-8.

Genck, Make the Most of Antisolvent Crystallization; A Number of Factors Can Affect Solids' Formation, Available Online at: https://www.chemicalprocessing.com/articles/2010/210/, Nov. 8, 2010, 8 pages.

(56) References Cited

OTHER PUBLICATIONS

Gettys et al., RU-486 (Mifepristone) Ameliorates Diabetes but Does Not Correct Deficient β-Adrenergic Signalling in Adipocytes from Mature C57BL/6J-ob/ob Mice, International Journal of Obesity, vol. 21, No. 10, Oct. 1997, pp. 865-873.
Green et al., Weight Gain from Novel Antipsychotic Drugs: Need for Action, General Hospital Psychiatry, vol. 22, No. 4, Jul.-Aug. 2000, pp. 224-235.
Greicius et al., Presenile Dementia Syndrome: An Update on Taxonomy and Diagnosis, Journal of Neurol, Neurosurg, Psychiatry, vol. 72, 2002, pp. 691-700.
Gupta et al., Studies on Carboxylation in Heterocyclic Systems, Journal of Scientific and Industrial Research, vol. 20B, Aug. 1961, pp. 394-397.
Highlights of Prescribing Information, KORLYM® (Mifepristone), Concept Therapeutics Incorporated, 2017, 7 pages.
Hsin et al., Stereoselective Synthesis of Morphine Fragments Trans- and Cis-Octahydro-1H-Benzo [4,5] Furo[3,2-e]Isoquinolines, Elsevier Lmitited, Tetrahedron, vol. 61, No. 2, Jan. 10, 2005, pp. 513-520.
Hunt et al., Identification of the Clinical Candidate (R)-(1-(4-Fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone (CORT125134): A Selective Glucocorticoid Receptor, Journal of Medicinal Chemistry, vol. 60, No. 8, Apr. 3, 2017, pp. 3405-3421.
Johnson et al., Relationships Between Drug Activity in NCI Preclinical in Vitro and in Vivo Models and Early Clinical Trials, British Journal of Cancer, vol. 84, No. 10, May 18, 2001, pp. 1424-1431.
Kugita, Studies on the Syntheses of Hydrogenated Quinolines and Isoquinolines as Analgesics, Pharmaceutical Bulletin, vol. 4, No. 1, Feb. 1956, pp. 29-34.
Magee et al., Construction of Cis- and Trans- Decahydroisoquinolines Via Heterogeneous Catalytic Hydrogenation, The Journal of Organic Chemistry, American Chemical Society, vol. 64, No. 7, Mar. 16, 1999, pp. 2549-2554.
Mahmood et al., 3D-QSAR Comfa, Comsia Studies on Pyrazolo-Fused Azadecalins Derivatives as Selective Glucocorticoid Receptor Antagonists, Pharma Science Monitor, vol. 3, Issue 3, Jul. 2012, pp. 2027-2055.
Melkersson et al., Insulin and Leptin Levels in Patients with Schizophrenia or Related Psychoses-a Comparison Between Different Antipsychotic Agents, Psychopharmacology, vol. 154, No. 2, Mar. 1, 2001, pp. 205-212.
Nakawatase et al., Alzheimer's Disease and Related Dementia, Cecil's Textbook of Medicine, Twenty-First Edition, vol. 1. W. B. Saunders Company, 2000, pp. 2042-2045.
Rehn et al., Antiinflammatory Action of Glucocorticoids—New Mechanisms for Old Drugs, The New England Journal of Medicine, vol. 353, No. 16, Oct. 20, 2005, pp. 1711-1723.
Rigalleau et al., Diabetes as a Result of Atypical Anti-Psychotic Drugs-a Report of Three Cases, Diabetic Medicine, vol. 17, No. 6, Jun. 2000, pp. 484-486.
Sausville et al., Contributions of Human Tumor Xenografts to Anticancer Drug Development, Cancer Research, vol. 66, No. 7, Apr. 2006, pp. 3351-3354.
Schultz et al., Heteroatom Directed Photoarylation. Synthetic Potential of the Heteroatom Oxygen, Journal of the American Chemical Society, vol. 100, No. 7, Mar. 29, 1978, pp. 2150-2162.
Schultz et al., Studies Directed at a Synthesis of the Morphine Alkaloids. A Photochemical Approach, The Journal of Organic Chemistry, vol. 50, No. 2, Jan. 1985, pp. 217-231.
Spitz et al., Mifepristone (RU 486)—A Modulator of Progestin and Glucocorticoid Action, The New England Journal of Medicine, Massachusetts Medical Society, vol. 329, No. 6, Aug. 5, 1993, pp. 404-412.
Teutsch et al., Design of Ligands for the Glucocortoid and Progestin Receptors, Biochemical Society Transactions, vol. 19, No. 4, Nov. 1991, pp. 901-908.
U.S. Appl. No. 12/777,340, Declaration Under 37 CFR 1.132 by Robin Clark, Solid Forms and Process for Preparing mailed on Feb. 2013, 5 pages.
U.S. Appl. No. 14/549,885, Octahydro Fused Azadecalin Glucocorticoid Receptor Modulators filed on Nov. 21, 2014, 91 pages.
U.S. Appl. No. 14/549,885, First Hunt Declaration mailed on Jan. 18, 2017, pp. 1-4.
U.S. Appl. No. 14/549,885, Second Hunt Declaration mailed on Jul. 7, 2017, 14 pages.
U.S. Appl. No. 16/036,001, Octahydro Fused Azadecalin Glucocorticoid Receptor Modulators filed on Jul. 16, 2018, 91 pages.
U.S. Appl. No. 16/161,642, Octahydro Fused Azadecalin Glucocorticoid Receptor Modulators filed on Oct. 16, 2018, 107 pages.
Uchida et al., An Efficient Access to the Optically Active Manzamine Tetracyclic Ring System, Tetrahedron Letters, vol. 40, Issue 1, Jan. 1, 1999, pp. 113-116.
Bofelli et al., "Glucocorticold Antagonists Improve Insulin Sensitivity in Mice", 741•P, Obesity, Integrative Physiology of Obesity, vol. 18, Supplement 2, Nov. 2010, 1 page.
Chinese Patent Application No. 202080086165.9, "Office Action", dated May 8, 2023, 13 pages.
Park, "Corcept Therapeutics Announces Third Quarter 2019 Financial Results and Provides Corporate Update", https://ir.corcept.com/news-releases/news-release-details/corcept-therapeutics-announces-third-quarter-2019-financial, Nov. 7, 2019, pp. 1-10.
Belanoff et al., "Selective Glucocorticoid Receptor (Type II) Antagonistprevents and Reverses Olanzapine-induced Weight Gain", Diabetes, Obesity and Metabolism, vol. 12, No. 2, Apr. 20, 2010, pp. 545-547.
Belanoff et al., "Selective Glucocorticoid Receptor {Type II) Antagonists Prevent Weight Gain Caused by Olanzapine in Rats", European Journal of Pharmacology, vol. 655, No. 1-3, Mar. 25, 2011, pp. 117-120.
Chilean Patent Application No. 202201250 , "Office Action", dated Nov. 29, 2023, 9 pages.
European Patent Application No. 20900160.1 , "Extended European Search Report", dated Dec. 1, 2023, 11 pages.
Gross et al., "Mifepristone Reduces Weight Gain and Improves Metabolic Abnormalities Associated With Risperidone Treatment in Normal Men", Obesity, vol. 18, No. 12, Dec. 1, 2010, pp. 2295-2300.
Gross et al., "Mifepristone Treatment of Olanzapine-induced Weight Gain in Healthy Men", Advances in Therapy, vol. 26, No. 10, Oct. 1, 2009, pp. 959-969.
Hunt et al., "Discovery of a Novel Non-Steroidal GR Antagonist with in Vivo Efficacy in the Olanzapine-Induced Weight Gain Model in the Rat", Bioorganic & Medicinal Chemistry Letters, vol. 22, No. 24, Dec. 15, 2012, pp. 7376-7380.
Lee et al., "Reversal of Antipsychotic-induced Weight Gain in Rats With Miricorilant, a Selective Glucocorticoid Receptor (GR) Modulator", Prepared for the American Psychiatric Association Annual Meeting, Apr. 25-29, 2020, 1 page.
Sindelar et al., "LLY-2707, A Novel Nonsteroidal Glucocorticoid Antagonist That Reduces Atypical Antipsychotic- Associated. Weight Gain in Rats", Journal of Pharmacology and Experimental Therapeutics, vol. 348, No. 1, Jan. 1, 2014,.

* cited by examiner

METHODS OF TREATING ANTIPSYCHOTIC-INDUCED WEIGHT GAIN WITH MIRICORILANT

CROSS-REFERENCE TO RELATED APPLICATIONS

This application claims priority to, and the benefit of, U.S. Provisional Patent Application Ser. No. 62/946,957, filed Dec. 11, 2019, the entire contents of which is hereby incorporated by reference in its entirety.

BACKGROUND

Administration of antipsychotic medication is an important treatment for many psychiatric disorders, and provides significant relief to the nearly 20 million patients suffering from such disorders. Unfortunately, antipsychotic medications such as olanzapine, risperidone, clozapine, quetiapine, aripiprazole, sertindole, and other such medications, often lead to significant weight gain as well as alleviating psychotic symptoms. Antipsychotic-induced weight gain is a significant problem for patients taking antipsychotic medications. Numerous reports indicate that about 40-80% of patients who receive antipsychotic medications for long periods of time experience substantial weight gain, ultimately exceeding their ideal body weight by 20% or more (see, e.g., Umbricht et al., J Clin. Psychiatry 55 (Suppl. B):157-160, 1994; Baptista, Acta Psychiatr. Scand. 100:3-16, 1999). Such weight gain increases the risk of many serious health problems associated with obesity, such as cardiovascular disease, stroke, hypertension, type II diabetes, and certain types of cancer. In addition, unwanted weight gain is one of the most common reasons for a patient's non-compliance with the administration of antipsychotic medications. Management strategies such as switching medications, lifestyle modifications, and the use of metformin have had modest and mixed results on these patients' weight. However, due to the poor results from these strategies, this serious health problem faced by those in need of antipsychotic medication remains unsolved.

Accordingly, there is need in the art for methods and medications that prevent or reduce the weight gain associated with use of antipsychotic medications, and that reverse the weight gain caused by such medications.

SUMMARY

Applicant discloses herein that administration of miricorilant, a glucocorticoid receptor (GR) modulator (GRM) can reduce antipsychotic-induced weight gain, can ameliorate the effects of antipsychotic-induced weight gain, and can reverse antipsychotic-induced weight gain. The patient may continue to receive antipsychotic medication while receiving miricorilant and still receive the benefits of miricorilant treatment. Antipsychotic medications which may induce weight gain, and the effects of which may be ameliorated, reduced or reversed by miricorilant treatment, include olanzapine, risperidone, clozapine, quetiapine, sertindole, amisulpride, aripiprazole, asenapine, blonanserin, bifeprunox, cariprazine, clotiapine, iloperidone, lurasidone, mosapramine, melperone, paliperidone, perospirone, pimavanserin, remoxipride, sulpiride, ziprasidone, zotepine, perphenazine, thioridazine, chlorpromazine and other such weight-inducing antipsychotic medications.

Benefits of the methods and treatments disclosed herein include reduced weight gain, reduced rate of weight gain, reversal of weight gain, reduction in risk of developing cardiovascular disease, stroke, hypertension, and type II diabetes. Thus, the present methods can reduce or reverse antipsychotic-induced weight gain, and can provide reduction in risk factors associated with weight gain (e.g., high blood pressure, high cholesterol, other blood lipid abnormalities, sleep disorders, insulin resistance, etc.).

The methods include administration of miricorilant (also known as CORT118335) to a patient receiving, or who has received, or who is expected to receive, an antipsychotic drug such as olanzapine, risperidone, clozapine, quetiapine, sertindole, amisulpride, aripiprazole, asenapine, blonanserin, bifeprunox, cariprazine, clotiapine, iloperidone, lurasidone, mosapramine, melperone, paliperidone, perospirone, pimavanserin, remoxipride, sulpiride, ziprasidone, zotepine, perphenazine, thioridazine, chlorpromazine, and other such weight-inducing antipsychotic medications. Miricorilant may be orally administered. The methods may reduce the amount of weight that the patient would otherwise have gained. The methods may reduce the rate of weight gain that the patient would otherwise have experienced. The methods may prevent weight gain in a patient administered antipsychotic medication. The methods may reverse weight gain that the patient experienced due to administration of antipsychotic medication.

Miricorilant is a cyclohexyl pyrimidine compound, that is, miricorilant is a GRM compound comprising a pyrimidine cyclohexyl structure, wherein the structure is as described and disclosed in U.S. Pat. No. 8,685,973, the entire contents of which is hereby incorporated by reference in its entirety. Miricorilant is (E)-6-(4-Phenylcyclohexyl)-5-(3-trifluoromethylbenzyl)-1H-pyrimidine-2,4-dione, which has the structure:

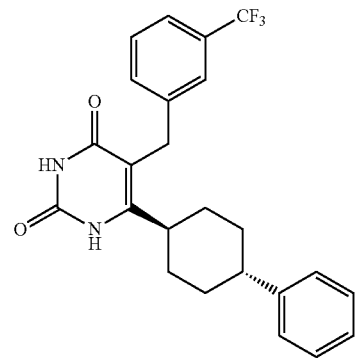

Other GRM compounds comprising a pyrimidine cyclohexyl structure, as disclosed, for example, in U.S. Pat. No. 8,685,973, may also be suitable for, and useful for, treating a subject suffering from antipsychotic-induced weight gain and for treating a subject suspected of being at risk of suffering antipsychotic-induced weight.

DETAILED DESCRIPTION

Figure 1:
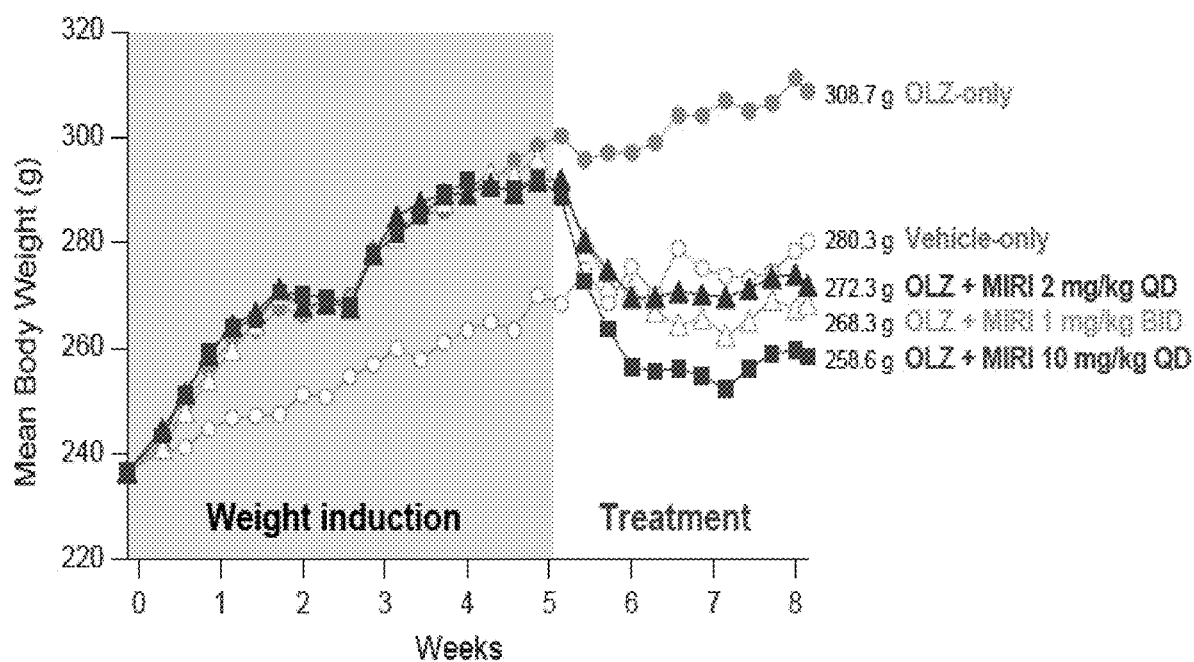
FIG. 1 shows the effect of olanzapine on weight gain in rats (weights shown as mean values).

Methods and compositions for treating a subject at risk of, or suffering from antipsychotic-induced weight gain are disclosed. The methods include administration of a cyclohexyl pyrimidine glucocorticoid receptor modulator (GRM) such as miricorilant (CORT118335) to a patient receiving, or who has received, or who is expected to receive, an antipsychotic drug such as olanzapine, risperidone, clozapine, or other weight-inducing antipsychotic medication. The GRM (e.g., miricorilant) may be orally administered. Administration of such a GRM along with antipsychotic medication may reduce the amount of weight, or reduce the rate of weight gain, or prevent weight gain, otherwise due to antipsychotic medication alone. The methods may reverse weight gain in a patient previously administered antipsychotic medication. Administration of such a GRM with antipsychotic medication may reduce, or reduce gain in, or prevent gain in, or reverse gain in, insulin resistance or blood levels of liver enzymes (AST, ALT), triglycerides, or insulin. Thus, in embodiments, the methods disclosed herein comprise administration of an effective amount of miricorilant to a patient at risk of suffering from antipsychotic-induced weight gain, thereby reducing the risk of antipsychotic-induced weight gain in that patient. Patients at risk of suffering from antipsychotic-induced weight gain include patients who have not yet been, but are expected to be, administered a weight-inducing antipsychotic medication; patients who are currently being administered a weight-inducing antipsychotic medication; patients who have been administered a weight-inducing antipsychotic medication; and other such patients.

In embodiments, the methods disclosed herein comprise administration of an effective amount of miricorilant to a patient who suffers from antipsychotic-induced weight gain, thereby ameliorating the effects of antipsychotic-induced weight gain in that patient. In embodiments, the methods disclosed herein comprise administration of an effective amount of miricorilant to a patient who suffers from antipsychotic-induced weight gain, thereby reducing antipsychotic-induced weight gain in that patient as compared to the weight gain expected to occur in the absence of miricorilant treatment. In embodiments, the methods disclosed herein comprise administration of an effective amount of miricorilant to a patient who suffers from antipsychotic-induced weight gain, thereby reducing weight previously gained due to antipsychotic-induced weight gain in that patient, effect to reverse antipsychotic-induced weight gain. In embodiments, a portion of the weight gain is reversed; in embodiments, the portion is about 1%, 2%, 3%, 4%, 5%, 7%, or 10% of the antipsychotic-induced weight gain in that patient; in other embodiments, about a quarter of the weight gained due to antipsychotic-induced weight gain is reversed; in further embodiments, about a half of the weight gained due to antipsychotic-induced weight gain is reversed; in yet further embodiments, more than half of the weight gained due to antipsychotic-induced weight gain is reversed. Patients who suffer from antipsychotic-induced weight gain include patients who have been administered a weight-inducing antipsychotic medication; patients who are currently being administered a weight-inducing antipsychotic medication; and other such patients.

In embodiments, the methods disclosed herein comprise administration of an effective amount of miricorilant to a patient who suffers from antipsychotic-induced weight gain, thereby reducing the amount of antipsychotic-induced weight gain in that patient. In embodiments, reducing the amount of antipsychotic-induced weight gain in that patient includes reducing the number of pounds gained by the patient as compared to the patient's weight prior to, or at the initiation of, administration of antipsychotic medication. In embodiments, the methods disclosed herein comprise administration of an effective amount of miricorilant to a patient who suffers from antipsychotic-induced weight gain, thereby reducing the rate of antipsychotic-induced weight gain in that patient (e.g., reducing the number of pounds per day, or pounds per week, or pounds per month, gained by the patient as compared to the rate of weight gain due to antipsychotic medication prior to miricorilant administration). Patients who suffer from antipsychotic-induced weight gain include patients who have been administered a weight-inducing antipsychotic medication; patients who are currently being administered a weight-inducing antipsychotic medication; and other such patients.

In embodiments, the methods disclosed herein comprise administration of an effective amount of miricorilant to a patient who has gained weight due to prior administration of antipsychotic medication, thereby reversing the antipsychotic-induced weight gain in that patient.

Methods and compositions for treating a subject suffering from antipsychotic-induced weight gain are disclosed. Methods and compositions for treating a subject suspected of being at risk of suffering antipsychotic-induced weight gain are disclosed (e.g., due to present or planned administration of antipsychotic medication). The methods include administration of miricorilant (also known as CORT118335) to a patient receiving, or who has received, or who is expected to receive, an antipsychotic drug such as olanzapine, risperidone, clozapine, quetiapine, sertindole, amisulpride, aripiprazole, asenapine, blonanserin, bifeprunox, cariprazine, clotiapine, iloperidone, lurasidone, mosapramine, melperone, paliperidone, perospirone, pimavanserin, remoxipride, sulpiride, ziprasidone, zotepine, perphenazine, thioridazine, chlorpromazine and other such weight-inducing antipsychotic medications. The methods may reduce the amount of weight that the patient would otherwise have gained. The methods may reduce the rate of weight gain that the patient would otherwise have experienced. The methods may prevent weight gain in a patient administered antipsychotic medication. The methods may reverse weight gain that the patient experienced due to administration of antipsychotic medication.

Miricorilant is a cyclohexyl pyrimidine compound, that is, miricorilant is a GRM compound comprising a pyrimidine cyclohexyl structure, wherein the structure is as described and disclosed in U.S. Pat. No. 8,685,973, the entire contents of which is hereby incorporated by reference in its entirety. Miricorilant is (E)-6-(4-Phenylcyclohexyl)-5-(3-trifluoromethylbenzyl)-1H-pyrimidine-2,4-dione, which has the structure:

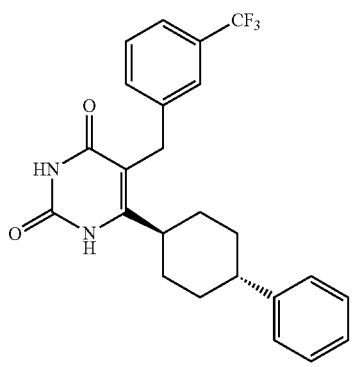

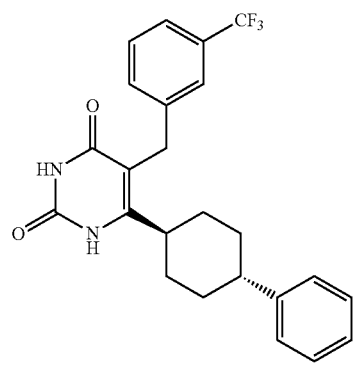

Other GRM compounds comprising a pyrimidine cyclohexyl structure, as disclosed, for example, in U.S. Pat. No. 8,685,973, may also be suitable for, and useful for, treating a subject suffering from antipsychotic-induced weight gain and for treating a subject suspected of being at risk of suffering antipsychotic-induced weight.

In some cases, miricorilant (or other GRM compounds comprising a pyrimidine cyclohexyl structure) is orally administered.

Accordingly, Applicant discloses methods of treating a subject suffering from antipsychotic-induced weight gain, comprising administering to the subject an effective amount of a cyclohexyl pyrimidine glucocorticoid receptor modulator (GRM) while said subject is administered an antipsychotic medication, wherein said treatment is effective to: reduce the body weight of a subject, as compared to baseline body weight of said subject prior to said administration of said GRM, wherein the subject has previously been administered an antipsychotic medication; or reduce the weight gain of a subject over time while taking an antipsychotic medication and said GRM, as compared to average weight gain of subjects taking that antipsychotic medication in the absence of the GRM; or reduce blood levels of triglycerides as compared to triglyceride levels in the blood of said subject prior to said administration of said GRM, wherein the subject has previously been administered an antipsychotic medication; or reduce blood levels of the liver enzymes ALT, AST, or both as compared to baseline liver enzyme levels in the blood of said subject prior to said administration of said GRM, wherein the subject has previously been administered an antipsychotic medication; or reduce plasma insulin level as compared to the baseline plasma insulin level of said subject prior to said administration of said GRM, wherein the subject has previously been administered an antipsychotic medication; or reduce insulin resistance as compared to baseline insulin resistance of said subject prior to said administration of said GRM, wherein the subject has previously been administered an antipsychotic medication (as measured by HOMA-IR or HOMA2-IR); or combinations thereof.

In embodiments of the methods of treating a subject suffering from antipsychotic-induced weight gain, the cyclohexyl pyrimidine glucocorticoid receptor modulator (GRM) is (E)-6-(4-Phenylcyclohexyl)-5-(3-trifluoromethylbenzyl)-1H-pyrimidine-2,4-dione (also termed miricorilant), which has the structure:

In embodiments of the methods, treatment comprises ameliorating the effects of antipsychotic-induced weight gain in the patient. In embodiments of the methods, treatment comprises reducing the effects of antipsychotic-induced weight gain in the patient. In embodiments of the methods, treatment comprises reducing the amount of antipsychotic-induced weight gain in the patient. In embodiments of the methods, treatment comprises reducing the rate of antipsychotic-induced weight gain in the patient. In embodiments of the methods, treatment comprises reversing the antipsychotic-induced weight gain in the patient, whereby said patient loses weight.

Applicant discloses herein methods of treating a subject at risk of suffering from antipsychotic-induced weight gain, the method comprising administering to the subject an effective amount of a cyclohexyl pyrimidine glucocorticoid receptor modulator (GRM) while said subject is administered an antipsychotic medication, wherein the subject has not previously been administered an antipsychotic medication, and wherein said treatment is effective to: reduce the weight gain of a subject over time while taking said antipsychotic medication and said GRM, as compared to average weight gain of subjects administered that antipsychotic medication in the absence of the GRM; or reduce the increase in blood levels of triglycerides as compared to the average increase in triglyceride levels in the blood of subjects administered said antipsychotic medication; or reduce the increase in blood levels of liver enzymes ALT or AST, or both, as compared to the average increase in said liver enzyme levels in the blood of subjects administered said antipsychotic medication; or reduce the increase in plasma insulin level as compared to the average increase in plasma insulin level in subjects administered said antipsychotic medication; or reduce the increase in insulin resistance (as measured by HOMA-IR or HOMA2-IR) as compared to the average increase in insulin resistance of in subjects administered said antipsychotic medication; or combinations thereof.

In embodiments of the methods of treating a subject at risk of suffering from antipsychotic-induced weight gain, the cyclohexyl pyrimidine glucocorticoid receptor is (E)-6-(4-Phenylcyclohexyl)-5-(3-trifluoromethylbenzyl)-1H-pyrimidine-2,4-dione (also known as miricorilant), which has the structure:

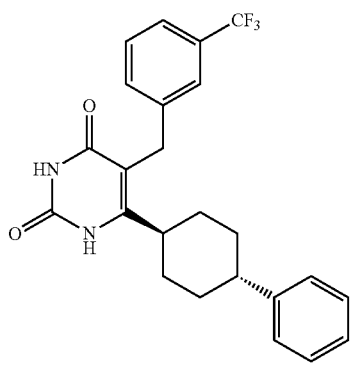

In embodiments of the methods treating a subject at risk of suffering from antipsychotic-induced weight gain, treatment comprises ameliorating the effects of antipsychotic-induced weight gain in the patient. In embodiments of the methods treating a subject at risk of suffering from antipsychotic-induced weight gain, treatment comprises reducing the effects of antipsychotic-induced weight gain in the patient. In embodiments of the methods treating a subject at risk of suffering from antipsychotic-induced weight gain, treatment comprises reducing the amount of antipsychotic-induced weight gain in the patient. In embodiments of the methods treating a subject at risk of suffering from antipsychotic-induced weight gain, treatment comprises reducing the rate of antipsychotic-induced weight gain in the patient. In embodiments of the methods treating a subject at risk of suffering from antipsychotic-induced weight gain, treatment comprises reversing the antipsychotic-induced weight gain in the patient, whereby said patient loses weight as compared to the patient's weight prior to administration of said GRM.

In embodiments of any of the methods disclosed herein, said GRM administration may comprise oral administration of said GRM; said GRM may be miricorilant. In embodiments of the methods of treating a subject suffering from antipsychotic-induced weight gain, treatment may comprise concomitant administration of an antipsychotic medication and an GRM (e.g., miricorilant), and the treatment may be effective to reduce one or more of body weight, weight gain, liver enzyme levels in the blood, plasma insulin, and insulin resistance (HOM-IR or HOMA2-IR) by about 10%, or 20%, or 25%, or 30%, or 35%, 05 40%, or 45%, or more.

In embodiments of any of the methods of treating a subject at risk of suffering from antipsychotic-induced weight gain, said treatment comprising concomitant administration of an antipsychotic medication and an GRM (e.g., miricorilant), and the treatment may be effective to reduce one or more of weight gain, liver enzyme levels in the blood, plasma insulin, and insulin resistance (HOM-IR or HOMA2-IR) by about 10% or 20%, or 25%, or 30%, or 35%, 05 40%, or 45%, or more.

B. Definitions

As used herein, the terms "subject" and "patient" refer to a human that is or will be receiving, or has received, a treatment (e.g., administration of miricorilant or other cyclohexyl pyrimidine GRM compound) disclosed herein. A patient is a subject in need of, or receiving, medical treatment for a disease or condition.

As used herein, the terms "administer," "administering," "administered" or "administration" refer to providing a compound or a composition (e.g., one described herein), to a subject or patient. For example, a compound or composition may be administered orally to a patient.

As used herein, the term "effective amount" or "therapeutic amount" refers to an amount of a pharmacological agent effective to treat, eliminate, or mitigate at least one symptom of the disease being treated. In some cases, "therapeutically effective amount" or "effective amount" can refer to an amount of a functional agent or of a pharmaceutical composition useful for exhibiting a detectable therapeutic or inhibitory effect. The effect can be detected by any assay method known in the art.

As used herein, the terms "administer," "administering," "administered" or "administration" refer to providing a compound or a composition (e.g., one described herein), to a subject or patient. Administration may be by oral administration (i.e., the subject receives the compound or composition via the mouth, as a pill, capsule, liquid, or in other form suitable for administration via the mouth. Oral administration may be buccal (where the compound or composition is held in the mouth, e.g., under the tongue, and absorbed there). Administration may be by injection, i.e., delivery of the compound or composition via a needle, microneedle, pressure injector, or other means of puncturing the skin or forcefully passing the compound or composition through the skin of the subject. Injection may be intravenous (i.e., into a vein); intraarterial (i.e., into an artery); intraperitoneal (i.e., into the peritoneum); intramusucular (i.e., into a muscle); or by other route of injection. Routes of administration may also include rectal, vaginal, transdermal, via the lungs (e.g., by inhalation), subcutaneous (e.g., by absorption into the skin from an implant containing the compound or composition), or by another route.

As used herein, the term "compound" is used to denote a molecular moiety of unique, identifiable chemical structure. A molecular moiety ("compound") may exist in a free species form, in which it is not associated with other molecules. A compound may also exist as part of a larger aggregate, in which it is associated with other molecule(s), but nevertheless retains its chemical identity. A solvate, in which the molecular moiety of defined chemical structure ("compound") is associated with a molecule(s) of a solvent, is an example of such an associated form. A hydrate is a solvate in which the associated solvent is water. The recitation of a "compound" refers to the molecular moiety itself (of the recited structure), regardless of whether it exists in a free form or an associated form.

As used herein, the term "composition" is intended to encompass a product comprising the specified ingredients such as the compound miricorilant, its tautomeric forms, derivatives, analogues, stereoisomers, polymorphs, deuterated species, pharmaceutically acceptable salts, esters, ethers, metabolites, mixtures of isomers, pharmaceutically acceptable solvates and pharmaceutically acceptable compositions in specified amounts, as well as any product which results, directly or indirectly, from combination of the specified ingredients in the specified amounts. Such term in relation to a pharmaceutical composition is intended to encompass a product comprising the active ingredient (s), and the inert ingredient (s) that make up the carrier, as well as any product which results, directly or indirectly, in combination, complexation or aggregation of any two or more of the ingredients, or from dissociation of one or more of the ingredients, or from other types of reactions or interactions of one or more of the ingredients. Accordingly, the pharmaceutical compositions of the present invention are meant to encompass any composition made by admixing miricorilant and pharmaceutically acceptable carriers.

"Pharmaceutically-acceptable excipient" and "pharmaceutically-acceptable carrier" refer to a substance that aids the administration of an active agent to—and absorption by—a subject and can be included in the compositions of the present invention without causing a significant adverse toxicological effect on the patient. As used herein, these terms are intended to include any and all solvents, dispersion media, coatings, antibacterial and antifungal agents, antioxidant agents, isotonic and absorption delaying agents, and the like, compatible with pharmaceutical administration. Non-limiting examples of pharmaceutically-acceptable excipients include water, NaCl, normal saline solutions, lactated Ringer's, normal sucrose, normal glucose, binders, fillers, disintegrants, encapsulating agents, plasticizers, lubricants, coatings, sweeteners, flavors and colors, and the like. One of ordinary skill in the art will recognize that other pharmaceutical excipients are useful in the present invention. The use of such media and agents for pharmaceutically active substances is well known in the art. Except insofar as any conventional media or agent is incompatible with the active compound, use thereof in the compositions is contemplated. Supplementary active compounds can also be incorporated into the compositions. One of ordinary skill in the art will recognize that other pharmaceutical excipients are useful in the present invention.

As used herein, the term "body weight" refers to the weight of a subject, e.g., the weight in kilograms (kg). A related term is the body mass index (BMI), which may be reported in units of kilograms per square meter (kg/m$^2$) where the square meter refers to body surface area. Body weight increases following administration of antipsychotic medication varies by the medication itself, and from individual to individual; however, over a period of ten weeks, mean increases of 4.45 kilograms (kg; clozapine), 4.15 kg (olanzapine), 2.92 kg (sertindole), and 2.10 kg (risperidone), have been reported (Allison et al., Am J. Psychiatry 156 (11):1686-96 (1999)). Allison et al. 2001 (J Clin Psychiatry 62(Suppl 7):22-31) reported that patients gained about 4-4.5 kg after receiving clozapine or olanzapine for 10 weeks; patients gained about 7-8 kg after about 40 weeks of olanzapine administration, and patients receiving olanzapine averaged weight gains of about 12 kg in a year; patients receiving risperidone gained 2-3 kg over 8-12 weeks (e.g., about 2.5 kg with 10 weeks of risperidone treatment); and that patients receiving quetiapine gained about 3 kg after treatment for a "short time" and gained between about 2 kg-5.6 kg over "long-term" treatment. Thus, patients receiving antipsychotic drug treatment gain weight, and this weight gain from may continue for long periods of time during treatment. For example, people beginning to take antipsychotic medication may gain about 1%, or 2%, or 4%, or 5%, or 8%, or 10%, or 12%, or 15% of their baseline (prior to beginning antipsychotic medication) body weight over the one, or two, or three, or four, or five, or six months following beginning antipsychotic medication. Patients taking a GRM along with antipsychotic medication may gain less weight, or gain weight at a slower rate, than do patients taking antipsychotic medication without also taking a GRM. For example, people who have gained weight while taking antipsychotic medication (where their weight after taking antipsychotic medication but before GRM administration is their baseline weight) may slow their weight gain, or may stop gaining weight while continuing to take antipsychotic medication when also taking a GRM, or may reduce their body weight from their baseline weight by about 1%, or 2%, or 3%, or 4%, or 5%, or 6%, or 7%, or 8%, or 9%, or 10%, or 12%, or 15% as compared to their body weight at the initiation of GRM therapy over the one, or two, or three, or four, or five, or six months following beginning GRM therapy while continuing to take antipsychotic medication.

As used herein, the term "liver enzyme" refers to one or more of the enzymes active in the liver of a subject; liver enzymes include, without limitation, alanine aminotransferase (ALT) and aspartame aminotransferase (AST). Normal blood test results for ALT may be about 7 to 55 units per liter (U/L) and for AST may be about 8 to 48 U/L. Antipsychotic-induced increases in liver enzymes can be significant. For example, liver enzymes ALT and AST may increase by about 50%, or 75%, or 100%, 150%, or 200%, or 250%, or 300%, or 350%, or 400%, or 500%, or 600%, or 700%, or 750%, or 800%, or more above their baseline (prior to beginning antipsychotic medication) over the one, or two, or three, or four, or five, or six months following beginning antipsychotic medication. As disclosed herein, GRM administration to patients receiving antipsychotic medication can reduce the magnitude of the liver enzyme increase induced by antipsychotic medication, and may reduce liver enzyme levels when administered to patients who have previously been administered antipsychotic medication prior to beginning GRM administration while continuing to take antipsychotic medication.

As used herein, the term "plasma insulin" refers to the level of insulin in the blood (plasma portion) of a subject. Normal fasting blood test results for plasma insulin levels may be less than about 25 mIU/L (less than about 174 picomoles per liter (pmol/L)) (where mIU are milli-insulin concentration units). After glucose administration, normal plasma insulin levels may range from about 30 to 230 mIU/L (208 to 1597 pmol/L)) at about 30 minutes after glucose, and may range from about 20 to 275 mIU/L (125 to 1900 pmol/L)) about one hour after glucose administration. For example, plasma insulin level may increase by about 15%, or 20%, or 25%, or 40%, or 50%, or 75%, or 100%, or 125%, or 150%, or 175%, or 200%, or more above the baseline plasma insulin level (prior to beginning antipsychotic medication) over the one, or two, or three, or four, or five, or six months following beginning antipsychotic medication. As disclosed herein, GRM administration to patients receiving antipsychotic medication can reduce the magnitude of the plasma insulin level increase induced by antipsychotic medication, and may reduce plasma insulin levels when administered to patients who have previously been administered antipsychotic medication prior to beginning GRM administration while continuing to take antipsychotic medication.

As used herein, the term "insulin resistance" refers to a condition in which greater than normal amounts of insulin are required for glucose homeostasis. Insulin resistance may be assessed, for example, by homeostasis model assessment-insulin resistance. Insulin resistance may be measured by "homeostatic model assessment-insulin resistance" (HOMA-IR) (see, e.g., Matthews et al., Diabetologia 28:412-419 (1985), and Gitch et al., Indian J Endocrinol Metab 19(1):160-164 (2015)), and may be measured by the "homeostatic model assessment 2-insulin resistance" (HOMA2-IR) as discussed, for example, in Rudenski et al., Metabolism 40(9):908-917 (1991). HOMA-IR levels are indicators of health; Ausk et al. report increased all-cause mortality for persons whose HOMA-IR scores were greater 1.4 (those with HOMA-IR levels >1.4 had higher all-cause mortality than those in the lowest quartile (HOMA-IR scores in the lowest quartile were ≤1.4); Diabetes Care 33(6):1179-

1185 (2010)). Ebenbichler et al. (J. Clin. Psychiatry 64:1436-1439 (2003)) report that homeostasis model assessment insulin resistance (HOMA-IR) doubled in patients over 8 weeks of olanzapine treatment (from 1.3±0.5 to 2.6±1.4 mmol/mU·L), but was essentially unchanged in control subjects who did not receive olanzapine (Table 1, page 1438). For example, HOMA-IR or HOMA2-IR may increase by about 25%, or 50%, or 75%, or 100%, or 125%, or 150%, or 200%, or 250%, or more above their baseline levels (prior to beginning antipsychotic medication) over the one, or two, or three, or four, or five, or six months following beginning antipsychotic medication. Slowing, stopping, or reversing such an increase in HOMA-IR or HOMA2-IR values improves patient health and well-being. Reducing a patient's HOMA-IR or HOMA2-IR to 1.4 or less is believed to reduce the patient's mortality risk. As disclosed herein, GRM administration to patients receiving antipsychotic medication can reduce the magnitude of the HOMA2-IR increase induced by antipsychotic medication, and may reduce HOMA2-IR levels when administered to patients who have previously been administered antipsychotic medication prior to beginning GRM administration while continuing to take antipsychotic medication.

As used herein, the term "triglycerides" refers to the important components of body fat, that are also an important component of the blood. Triglycerides are triesters comprising three fatty acid moieties, which fatty acids may be the same or different in an individual triglyceride molecule. Blood triglycerides may be measured in blood tests, and are typically measured as part of a "lipid panel" which may also include measurement of cholesterol and related blood lipids. Normal triglyceride levels in adults may be, for example, 150 milligrams per deciliter (mg/dL; 1.7 millimoles per liter (mmol/L)) or less; levels greater than 150 mg/dL are considered borderline high, and levels greater than about 200 mg/dL are considered high. As stated in the prescribing information for olanzapine tablets, triglyceride levels increased by 20.8 mg/dL in adults treated with olanzapine for 12 weeks; and were increased by 18.7 mg/dL over 48 weeks. Nearly 40% of these adult patients had triglyceride increases of ≥50 mg/dL at 12 weeks, and more than 60% of adult patients had triglyceride increases of ≥50 mg/dL at 48 weeks. Since normal triglyceride levels are less than 150 mg/dL, a 50 mg/dL increase represents an increase of at least 33%. For example, triglycerides may increase by about 15%, or 25%, or 40%, or 50%, or 75%, or 100%, or 125%, or 150%, or more above baseline triglyceride levels (prior to beginning antipsychotic medication) over the one, or two, or three, or four, or five, or six months following beginning antipsychotic medication.

As used herein, terms such as an antipsychotic medication, antipsychotic medications, an "antipsychotic", and the like, refer to olanzapine, risperidone, clozapine, quetiapine, sertindole, amisulpride, aripiprazole, asenapine, blonanserin, bifeprunox, cariprazine, clotiapine, iloperidone, lurasidone, mosapramine, melperone, paliperidone, perospirone, pimavanserin, remoxipride, sulpiride, ziprasidone, zotepine, perphenazine, thioridazine, chlorpromazine and other such weight-inducing antipsychotic medications.

As used herein, the term "glucocorticoid receptor" ("GR") refers to one of the family of intracellular receptors which specifically bind to cortisol and/or cortisol analogs such as dexamethasone (See, e.g., Turner & Muller, J. Mol. Endocrinol. Oct. 1, 2005 35 283-292). The glucocorticoid receptor is also referred to as the cortisol receptor. The term includes isoforms of GR, recombinant GR and mutated GR. A cortisol receptor is a glucocorticoid receptor (GR), specifically the type II GR, which specifically binds cortisol and/or cortisol analogs such as dexamethasone (See, e.g., Turner & Muller, J. Mol. Endocrinol. Oct. 1, 2005 35 283-292).

A mineralocorticoid receptor (MR), also known as a type I glucocorticoid receptor (GR I), is activated by aldosterone in humans.

The term "glucocorticoid receptor modulator" (GRM) refers to any compound which modulates any biological response associated with the binding of GR to an agonist. For example, a GRM that acts as an agonist, such as dexamethasone, increases the activity of tyrosine aminotransferase (TAT) in HepG2 cells (a human liver hepatocellular carcinoma cell line; ECACC, UK). A GRM that acts as an antagonist, such as mifepristone, decreases the activity of tyrosine aminotransferase (TAT) in HepG2 cells. TAT activity can be measured as outlined in the literature by A. Ali et al, J. Med. Chem., 2004, 47, 2441-2452.

GRM compounds include compounds comprising a pyrimidine cyclohexyl backbone, such as miricorilant. Exemplary GRM compounds comprising a pyrimidine cyclohexenyl backbone include compounds disclosed in U.S. Pat. No. 8,685,973 and in PCT/US2019/035229, the entire contents of which are hereby incorporated by reference in their entireties. All patents, patent publications, and patent applications disclosed herein, both supra and infra, are hereby incorporated by reference in their entireties.

Exemplary glucocorticoid receptor modulators comprising a cyclohexyl pyrimidine structure include those described in U.S. Pat. No. 8,685,973; in U.S. Pat. Nos. 8,906,917; and 9,321,736. In embodiments, the cyclohexyl pyrimidine GRM is (E)-6-(4-Phenylcyclohexyl)-5-(3-trifluoromethylbenzyl)-1H-pyrimidine-2,4-dione (also known as "miricorilant" or as "CORT118335" or "MIRI"), which has the structure:

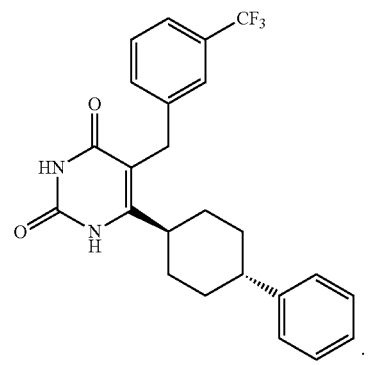 [SMILES: O=c1[nH]c(=O)c(Cc2cccc(C(F)(F)F)c2)c([C@H]2CC[C@H](c3ccccc3)CC2)[nH]1]

In some cases, the effective amount of the GRM (e.g., miricorilant) is a daily dose of between 1 and 20 milligrams per kilogram per day (mg/kg/day). In some embodiments, the daily dose of the GRM is 10, 20, 40, 60, 80, 100, 120, 140, 160, 180, 200, 300, 400, 500, 600, 700, 800, 900, 1000, 1100, 1200, 1300, 1400, 1500, 1750, or 2000 milligrams per day (mg/day). In some cases, the GRM is administrated for at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, or 80 weeks.

E. Glucocorticoid Receptor Modulators (GRM)

Administration of effective amounts of glucocorticoid receptor modulators (GRMs) is useful in the treatment of many diseases and disorders. GRMs useful in such treatments include nonsteroidal compounds comprising a pyrimidine cyclohexyl structure. In embodiments, the structure is as described and disclosed in U.S. Pat. No. 8,685,973, the entire contents of which is hereby incorporated by reference in its entirety. In embodiments, the compound comprising a pyrimidine cyclohexyl compound has the structure:

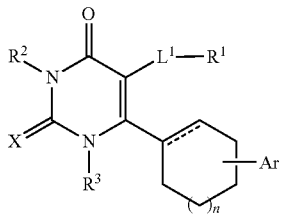

(I)

wherein
the dashed line is absent or a bond;
X is selected from the group consisting of O and S;
$R^1$ is selected from the group consisting of cycloalkyl, heterocycloalkyl, aryl and heteroaryl, optionally substituted with from 1 to 3 $R^{1a}$ groups;
each $R^{1a}$ is independently selected from the group consisting of H, $C_{1-6}$ alkyl, $C_{2-6}$ alkenyl, $C_{2-6}$ alkynyl, $C_{1-6}$ alkoxy, $C_{1-6}$ alkyl-$OR^{1b}$, halogen, $C_{1-6}$ haloalkyl, $C_{1-6}$ haloalkoxy, —$OR^{1b}$, —$NR^{1b}R^{1c}$, —$C(O)R^{1b}$, —$C(O)OR^{1b}$, —$OC(O)R^{1b}$, —$C(O)NR^{1b}R^{1c}$, —$NR^{1b}C(O)R^{1c}$, —$SO_2R^{1b}$, —$SO_2NR^{1b}R^{1c}$, cycloalkyl, heterocycloalkyl, aryl and heteroaryl;
$R^{1b}$ and $R^{1c}$ are each independently selected from the group consisting of H and $C_{1-6}$ alkyl;
$R^2$ is selected from the group consisting of H, $C_{1-6}$ alkyl, $C_{1-6}$ alkyl-$OR^{1b}$, $C_{1-6}$ alkyl-$NR^{1b}R^{1c}$ and $C_{1-6}$ alkylene-heterocycloalkyl;
$R^3$ is selected from the group consisting of H and $C_{1-6}$ alkyl;
Ar is aryl, optionally substituted with 1-4 $R^4$ groups;
each $R^4$ is independently selected from the group consisting of H, $C_{1-6}$ alkyl, $C_{1-6}$ alkoxy, halogen, $C_{1-6}$ haloalkyl and $C_{1-6}$ haloalkoxy;
$L^1$ is a bond or $C_{1-6}$ alkylene;
subscript n is an integer from 0 to 3,
and salts and isomers thereof.

In particular instances, the pyrimidine cyclohexyl compound is miricorilant, (E)-6-(4-Phenylcyclohexyl)-5-(3-trifluoromethylbenzyl)-1H-pyrimidine-2,4-dione which has the following structure:

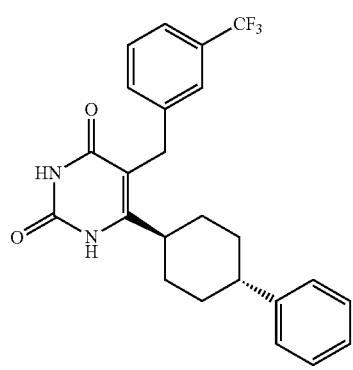

Pharmaceutical Compositions and Administration

Applicants disclose herein pharmaceutical compositions containing miricorilant. Oral preparations containing miricorilant may include tablets, tablets, powder, dragees, capsules, liquids, lozenges, gels, syrups, slurries, suspensions, etc., suitable for ingestion by the patient. Details on techniques for formulation and administration are well described in the scientific and patent literature, see, e.g., the latest edition of Remington's Pharmaceutical Sciences, Mack Publishing Co, Easton PA ("Remington's"). In powders, the carrier is a finely divided solid, which is in a mixture with the finely divided active component, such as miricorilant. In tablets, the active component is mixed with the carrier having the necessary binding properties in suitable proportions and compacted in the shape and size desired. The powders and tablets preferably contain from 5% or 10% to 70% of the active compound. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, tablets, cachets, and lozenges can be used as solid dosage forms suitable for oral administration.

Suitable solid excipients are carbohydrate or protein fillers that include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain GR modulator mixed with a filler or binders such as lactose or starches, lubricants such as talc or magnesium stearate, and, optionally, stabilizers. In soft capsules, the GR modulator compounds may be dissolved or suspended in suitable liquids, such as fatty oils, liquid paraffin, or liquid polyethylene glycol with or without stabilizers.

The pharmaceutical preparation is preferably in unit dosage form. In such form the preparation is subdivided into unit doses containing appropriate quantities of the active component, such as miricorilant. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 6000 mg, most typically 50 mg to 500 mg. Suitable dosages also include about 1 mg, 5, 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, or 2000 mg, according to the particular application and the potency of the active component. The composition can, if desired, also contain other compatible therapeutic agents.

In some embodiments, miricorilant is administered in one dose. In other embodiments, the GRM is administered in more than one dose, e.g., 2 doses, 3 doses, 4 doses, 5 doses, 6 doses, 7 doses, or more. In some cases, the doses are of an equivalent amount. In other cases, the doses are of different amounts. The doses can increase or taper over the duration of administration. The amount will vary according to, for example, patient characteristics.

The subject may be administered at least one dose of miricorilant in one or more doses over, for example, a 2-48 hour period. In some embodiments, miricorilant is administered as a single dose. In other embodiments, miricorilant is administered in more than one dose, e.g. 2 doses, 3 doses, 4 doses, 5 doses, or more doses over a 2-48 hour period, e.g., a 2 hour period, a 3 hour period, a 4 hour period, a 5 hour period, a 6 hour period, a 7 hour period, a 8 hour period, a 9 hour period, a 10 hour period, a 11 hour period, a 12 hour period, a 14 hour period, a 16 hour period, a 18 hour period, a 20 hour period, a 22 hour period, a 24 hour period, a 26 hour period, a 28 hour period, a 30 hour period, a 32 hour period, a 34 hour period, a 36 hour period, a 38 hour period, a 40 hour period, a 42 hour period, a 44 hour period, a 46 hour period or a 48 hour period. In some embodiments, the GRM is administered over 2-48 hours, 2-36 hours, 2-24 hours, 2-12 hours, 2-8 hours, 8-12 hours, 8-24 hours, 8-36 hours, 8-48 hours, 9-36 hours, 9-24 hours, 9-20 hours, 9-12 hours, 12-48 hours, 12-36 hours, 12-24 hours, 18-48 hours, 18-36 hours, 18-24 hours, 24-36 hours, 24-48 hours, 36-48 hours, or 42-48 hours.

Single or multiple administrations of formulations can be administered depending on the dosage and frequency as required and tolerated by the patient. The formulations should provide a sufficient quantity of miricorilant to effectively treat the disease state. Thus, in one embodiment, the pharmaceutical formulation for oral administration of miricorilant is in a daily amount of between about 1 to about 50 mg per kilogram of body weight per day (mg/kg/day), and may be, e.g., from about 2 mg/kg/day to about 20 mg/kg/day.

The duration of miricorilant treatment can vary according to the severity of the condition in a subject and the subject's response to miricorilant. In some embodiments, miricorilant can be administered for a period of about 1 week to 104 weeks (2 years), more typically about 2 weeks to about 80 weeks, most typically about 3 weeks to about 20 weeks. Generally administration of miricorilant should be continued until clinically significant reduction or amelioration is observed. Treatment with miricorilant may last for as long as two, three, four, five, six, seven, eight, nine, ten years or even longer.

In some embodiments, administration of miricorilant is not continuous and can be stopped for one or more periods of time, followed by one or more periods of time where administration resumes. Suitable periods where administration stops include 5 to 9 weeks, 5 to 16 weeks, 9 to 16 weeks, 16 to 24 weeks, 16 to 32 weeks, 24 to 32 weeks, 24 to 48 weeks, 32 to 48 weeks, 32 to 52 weeks, 48 to 52 weeks, 48 to 64 weeks, 52 to 64 weeks, 52 to 72 weeks, 64 to 72 weeks, 64 to 80 weeks, 72 to 80 weeks, 72 to 88 weeks, 80 to 88 weeks, 80 to 96 weeks, 88 to 96 weeks, and 96 to 100 weeks. Suitable periods where administration stops also include 5, 6, 7, 8, 9, 10, 11, 12, 13, 14, 15, 16, 17, 18, 19, 20, 24, 25, 30, 32, 35, 40, 45, 48 50, 52, 55, 60, 64, 65, 68, 70, 72, 75, 80, 85, 88 90, 95, 96, and 100 weeks.

Miricorilant can be used in combination with other active agents known to be useful in modulating a glucocorticoid receptor, or with adjunctive agents that may not be effective alone, but may contribute to the efficacy of the active agent.

After a pharmaceutical composition including miricorilant has been formulated, it can be placed in an appropriate container and labeled for treatment of an indicated condition. For administration of miricorilant, such labeling would include, e.g., instructions concerning the amount, frequency and method of administration.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill will readily recognize a variety of noncritical parameters which could be changed or modified to yield essentially similar results.

Example 1. Miricorilant Effect on Olanzapine-Induced Body Weight Gain in Rats

The effects of miricorilant on olanzapine-induced weight gain were assessed in female rats.

Antipsychotic-induced weight gain is a significant problem for patients taking second generation antipsychotic medications. Management strategies such as switching medications, lifestyle modifications, and use of metformin have had modest and mixed results on these patients' weight.

Miricorilant, a GR modulator without affinity for the progesterone receptor, has been reported to prevent olanzapine-induced weight gain in rats (Hunt et al., Bioorg Med Chem Lett. 22(24):7376-80 (2012)). Applicants disclose herein that miricorilant has the ability to reverse olanzapine-induced weight gain in rats.

Methods

To assess the effects of miricorilant on olanzapine-induced body weight gain, 60 female Sprague-Dawley rats were randomized into 5 treatment groups. Forty-eight female Sprague-Dawley rats received 2.4 mg/kg/day olanzapine (OLZ) for 34 days while on a normal diet. On day 35, the rodents were randomized to 4 different interventions and remained on study until day 57. The four intervention groups were: OLZ+vehicle daily by oral gavage; OLZ+2 mg/kg/day miricorilant once daily; OLZ+1 mg/kg miricorilant twice daily; and OLZ+10 mg/kg/day miricorilant once daily. A fifth group, a vehicle-only group (n=12), was included as a control for the entirety of the 57 days. Details of the study design are indicated in the following tables (Table A and Table B):

TABLE A

Study Design

| Group Number | Number of Female Animals | Induction[a] (Days 1 to 56) | Test Article Treatment (Days 35 to 57[b]) | Test Article Dose Level (mg/kg/dose)[c] | Test Article Frequency |
|---|---|---|---|---|---|
| 1 | 12 | Vehicle 1 | Vehicle 2 | 0 | BID |
| 2 | 12 | Olanzapine | Vehicle 2 | 0 | BID |
| 3 | 12 | Olanzapine | COR118335 | 1 | BID |
| 4 | 12 | Olanzapine | COR118335 | 2 | QD |
| 5 | 12 | Olanzapine | COR118335 | 10 | QD |

[a]The induction article and Vehicle 1 were administered twice daily (12 ± 1 hours apart) via oral gavage at a dose volume of 5 mL/kg/day (2.5 mL/kg/dose). The dose level for Olanzapine was 1.2 mL/kg/dose.
[b]Only one dose on Day 57.
[c]The test article and Vehicle 2 were administered via oral gavage BID or QD at a dose volume of 10 mL/kg/dose (5 mL/kg/dose or 10 mL/kg/dose, respectively).
BID: twice daily at 12 ± 1 hours apart
QD: once daily at 24 ± 2 hours apart

TABLE B

Group Assignments

| Group Number | Number of Female Animals | Induction | Test Article Treatment | Test Article Dose Level (mg/kg/dose) | Test Article Frequency |
|---|---|---|---|---|---|
| 1 | 12 | Vehicle 1 | Vehicle 2 | 0 | BID |
| 2 | 12 | Olanzapine | Vehicle 2 | 0 | BID |
| 3 | 12 | Olanzapine | COR118335 | 1 | BID |
| 4 | 12 | Olanzapine | COR118335 | 2 | QD |
| 5 | 12 | Olanzapine | COR118335 | 10 | QD |

BID: twice daily at 12 ± 1 hours apart
QD: once daily at 24 ± 2 hours apart

Weight gain was induced by administration of olanzapine (OLZ) over a 5-week period ("weight-induction phase"). Starting at week 6, either miricorilant (MIRI, 3 dosing regimens) or vehicle 2 was administered orally. Olanzapine administration was continued during this phase ("treatment phase"). The vehicle-only group was included as a control for the 8-week duration of the study. Efficacy was assessed based on body weight, food consumption, mortality, and clinical observations.

Vehicle 1 [1.5% (v/v) 1N hydrochloric acid, 1% (w/v) Cremophor EL, 97.5% sterile water for injection, USP] and the induction article (Olanzapine) were administered twice daily (12±1 hours apart) on Days 1 through 56 via oral gavage. The dose level for the induced groups was 1.2 mg/kg/dose at a dose volume of 2.5 mL/kg/dose (5 mL/kg/day). The vehicle group received Vehicle 1 in the same manner as the induced groups. Individual doses were based on the most recent body weights. Vehicle 1 and the induction article were administered prior to the Vehicle 2 and miricorilant (also termed "test article" or COR118335) on applicable dosing days. The articles were stored refrigerated between dosing. Vehicle 2 [10% (v/v) dimethyl sulfoxide, 0.1% (v/v) Tween 80, and 0.5% (w/v) hydroxypropyl methylcellulose, in sterile water for injection, USP] or miricorilant were administered on Days 35 through 57 via oral gavage. Animals in Groups 1 to 3 were administered Vehicle 2 or miricorilant twice daily (12±1 hours apart) at dose levels of 0 or 1 mg/kg/dose and a dose volume of 5 mL/kg/dose (10 mL/kg/day). Animals in Groups 4 and 5 were administered miricorilant once daily (24±2 hours apart) at dose levels of 2 or 10 mg/kg/dose and a dose volume of 10 mL/kg/dose (10 mL/kg/day). Individual doses were based on the most recent body weights. Vehicle 2 and miricorilant were continuously stirred during dosing, and the articles (vehicle, olanzapine, and miricorilant preparations) were stored refrigerated between dosing. On Day 57, only one dose was administered in the morning.

Body weights were measured and recorded three times weekly during the acclimation period, every other day beginning on Day −1, and prior to termination on Day 57. Food consumption was measured and recorded daily beginning on Day −14. Body weights and food consumption were measured within 2 hours of the initial time on Day −1. Any changes in bodyweight greater than 15 grams (g) and changes in food consumption greater than 5 g were verified. Food jars were weighed twice for precision during food jar changes.

The efficacy of miricorilant was assessed in female rats by three dose regimens which were 1 mg/kg/dose twice per day (BID: twice daily at 12±1 hours apart), 2 mg/kg/dose once per day (QD: once daily at 24±2 hours apart), and 10 mg/kg/dose QD after the induction of body weight gain by olanzapine for 5 weeks. During the acclimation period, normal body weight growth was observed with gains from group means in a range of 169 grams (g) to 174 g on Day −21 to that of 237 g on Day −1 at which time point animals were randomized into treatment groups. During olanzapine induction phase from Day 1 to Day 34 prior to the initiation of miricorilant treatment, group mean body weights increased similarly to 298, 296, 292, and 292 g at Day 34 for Groups 2 to 5 treated with olanzapine, respectively. These values were statistically significantly higher than 270 g in vehicle-only control Group 1, and represent body weight gains of 8 to 10% attributed to Olanzapine. Thus, as expected in this model, twice daily oral administration of olanzapine at 2.4 mg/kg/day significantly increased body weight and food consumption during the induction phase [Days 1 to 34 (Weeks 1 to 5)] in all olanzapine-treated groups and these effects were maintained throughout the remainder of the study period [Days 35 to 57 (Weeks 6 to 9)] in the olanzapine control group, compared to the vehicle-only control.

During the treatment phase from Day 35 to Day 57, group mean body weights in miricorilant-treated Groups 3 to 5 decreased to 269, 272, and 258 g with Least Squares (LS) mean values of 268, 272, and 259 g at Day 57, respectively, which were statistically significantly lower than that in the olanzapine control Group 2 (309 g) and represented reductions of 13%, 12% and 17% by miricorilant, respectively. This miricorilant-mediated body weight reduction effect became statistically significant starting on Days 36, 38, and 36 for Groups 3 to 5, respectively. It is noteworthy that the miricorilant treatment reduced body weights close to those observed in the vehicle-only control Group 1 within the first week of treatment and maintained this effect throughout the rest of the treatment period despite the presence of olanzapine. During the same treatment period, animals in the olanzapine control Group 2 continued to demonstrate weight gains that were statistically significantly higher than those in the vehicle-only control Group 1 and reached 309 g by Day 57, which is 29 g or 10% higher than that in Group 1 (280 g). There were no statistically differences in the miricorilant effects between the Low Dose (1 mg/dose) BID Group 3 and the Mid Dose (2 mg/dose) QD Group 4 whereas the High Dose (10 mg/dose) QD group 5 showed a statistically significantly greater weight reduction than the Low Dose BID Group 3 on Days 42, 44, 48, and 54 and the Mid Dose Group 4 on Days 40 to 57. Note that when comparing to Group 1, the group LS mean bodyweight in the High Dose QD Group 5 was also statistically significantly lower during Days 42 to 57 whereas the Low Dose BID Group 3 showed such effects but to a much lesser extent with statistical significance achieved only on Days 46 and 50. On Day 57, Groups 3 and 5 had body weights of 268 and 259 g, which were 4% and 8% lower than that in Group 1 (280 g) with statistical significance.

The oral administration of miricorilant completely abrogated the olanzapine-induced body weight gains and food consumption increases within the first week of the miricorilant treatment phase (Week 6) at all three dose regimens and maintained these effects during the treatment period. Miricorilant also caused a quick and steep decline in food consumption, such that food consumption in rats treated with miricorilant was lower than the basal level in the vehicle-only control group in that first week, but food consumption recovered to levels on a par with the basal level by Week 9 for all three dose regimens. The miricorilant-mediated body weight reduction leveled during Weeks 7 and 8 with a partial recovery during Weeks 8 to 9 to extents not beyond the basal body weight represented by the vehicle-only control. At the end of the study, the 10 mg/kg/dose QD regimen produced a loss of 8% compared with basal body weight whereas the 1 mg/kg/dose BID and 2 mg/kg/dose QD regimens had a loss of 4% or no significant loss, respectively. Thus, the Low Dose BID and High Dose QD regimens but not the Mid Dose QD regimen reduced basal body weight gains compared with the vehicle-treated rats, with the High Dose QD being the most prominent when comparing to the vehicle-only control. However, stabilization with a trend of recovery in body weights was observed with both Low Dose BID and High Dose QD groups during the last week of treatment (Days 50 to 57).

Food consumption in olanzapine-treated rats was normalized by the additional treatment with miricorilant. During the weight-induction phase (weeks 1-5), the mean increase in food consumption across the groups treated with olanzapine was 13%. The addition of miricorilant caused a normalization in food consumption to the vehicle-only levels by the end of the study. During the first week of treatment, food consumption in miricorilant-treated animals was 13%-20% lower when compared to the vehicle-only controls ($P<0.01$) and was 16%-23% lower when compared to olanzapine-only animals ($P<0.01$). Food consumption returned to vehicle-only levels by the end of the study for all three miricorilant dose regimens.

There were no mortalities nor miricorilant treatment-related adverse clinical signs besides signs expected for this model, such as body thinning and reduced feces output attributed to the miricorilant treatment-related reduction in body weight and food consumption. Terminal plasma concentrations of miricorilant were 61.43 (±21.81) and 69.47 (±24.87) ng/mL for the 1 mg/kg/dose BID and 2 mg/kg/dose QD regimens, respectively. For the 10 mg/kg/dose QD regimen, the miricorilant plasma concentration was 244.25 (±202.00) ng/mL or, after excluding an outlier sample value of 887 ng/mL from animal number 5503, 185.82 (±59.52) ng/mL. Based on the value of 185.82 ng/mL, exposure at the highest dose is approximately 3 or 4 fold higher than that at the lower doses. Thus, the miricorilant plasma levels are approximately proportional to its daily dose levels and consistent with the efficacy levels of miricorilant observed in this model. The similar plasma concentrations of miricorilant between the 1 mg/kg/dose BID and 2 mg/kg/dose QD regimens suggest that a daily single dose at 2 mg/kg was sufficient to achieve an exposure level comparable to that in the twice daily dose at 1 mg/kg/dose, consistent with the outcomes at the efficacy level.

Results

By day 34, the olanzapine treated groups had a higher mean body weight compared to the vehicle only control group (294.5 g vs 270 g, $p<0.05$). From days 35-57, the OLZ+vehicle group continued to gain weight. However, rats randomized to receive OLZ+miricorilant all had statistically significant ($p<0.05$) decreases in their weight by 12-17% compared to the OLZ+vehicle group. Weight loss in the miricorilant treated rats was immediate and sustained until the end of the study. All rodents remained healthy and active during the interventional phase with miricorilant or vehicle.

Summary and individual body weight data are illustrated in the FIG. 1, which shows the effect of olanzapine on weight gain in rats (weight shown as mean values).

In conclusion, miricorilant (CORT 118335) was effective in abrogation of olanzapine-induced gains in body weight in female rats. For all three dose regimens tested, miricorilant was effective in abrogation of olanzapine-induced gains in both body weight and food consumption with a daily dose dependency, in a good correlation with its systemic exposure levels. At the end of the treatment period, the 1 mg/kg/dose BID and 2 mg/kg/dose QD regimens showed a slight or no reduction compared with the basal body weight, respectively, whereas the 10 mg/kg/dose QD regimen resulted in a moderate reduction compared with basal body weight.

These results demonstrate that miricorilant was effective in reversing the weight gain associated with olanzapine in rats without the need for reduction or discontinuation of olanzapine.

Example 2. Miricorilant Attenuates Antipsychotic-Induced Weight Gain with Olanzapine in Healthy Male Human Subjects Antipsychotic medications such as olanzapine (OLZ) and risperidone (RSP) are commonly associated with significant weight gain leading to reduced quality of life, poor drug compliance, and increased cardiovascular morbidity and mortality. This example presents the results of a double-blind, placebo-controlled trial in healthy subjects, demonstrating that the glucocorticoid receptor modulator miricorilant (MIRI) significantly reduced the weight gain caused by the commonly prescribed antipsychotic medication olanzapine (OLZ; Zyprexa®).

Miricorilant (MIRI), a glucocorticoid receptor modulator without affinity for the progesterone receptor, has been demonstrated to prevent and reverse OLZ-induced weight gain in rats. The present study aims to demonstrate an attenuation of OLZ-induced weight gain by co-administration of MIRI+OLZ in healthy male subjects.

Antipsychotic medications such as olanzapine are essential to the health of millions of patients, but the weight gain and other metabolic side effects they cause are life-threatening and often lead patients to discontinue treatment. The dose level tested in our Phase 1b trial was 600 mg/day. At this dose, healthy subjects given olanzapine plus miricorilant gained less weight than subjects receiving olanzapine plus placebo (see Table 2). In addition, markers of liver damage that often rise temporarily at the start of olanzapine therapy increased less sharply in subjects receiving miricorilant, suggesting that miricorilant may have protective effects in the liver (see Table 2). Five subjects in the olanzapine alone group were unable to complete the study due to elevated liver enzymes, while one patient in the miricorilant group experienced this problem."

Methods

A 2-week, single-center, double-blind, randomized, placebo-controlled study was conducted in healthy male subjects age 18-55 years with BMI between 18-25 kg/m$^2$ and a stable body weight (defined as the Day 1 pre-dose body weight to be within ±2.0% of screening body weight). Sixty-six subjects were randomized 1:1 to receive either miricorilant (MIRI, 600 mg/day) or matching placebo (PBO) administered concomitantly with olanzapine (OLZ, 10 mg/day) for 14-days. Food was freely available to all subjects during the study. The difference in mean change in absolute body weight after administration of OLZ+PBO compared to OLZ+MIRI was evaluated using a repeated measures model with imputation applied to missing values.

TABLE 1

Baseline Characteristics of Study Participants

|  | OLZ + MIRI (n = 33) | OLZ + PBO (n = 33) |
|---|---|---|
| Age, years (mean ± SD) | 33.5 ± 11.6 | 29.0 ± 8.9 |
| Race, n (%) | | |
| Caucasian | 28 (84.8%) | 26 (78.8%) |
| Other | 5 (15.2%) | 7 (21.2%) |
| Weight, kg (mean ± SD) | 71.95 ± 5.57 | 71.43 ± 7.10 |
| BMI, kg/m$^2$ (mean ± SD) | 22.35 ± 1.48 | 22.89 ± 1.57 |
| Liver enzymes | | |
| ALT, IU/L (mean ± SD) (reference range: 10-50 IU/L in males) | 21.8 ± 6.1 | 22.8 ± 7.3 |
| AST, IU/L (mean ± SD) (reference range: 0-37 IU/L in males) | 23.3 ± 13.5 | 22.8 ± 4.4 |

TABLE 1-continued

Baseline Characteristics of Study Participants

|  | OLZ + MIRI (n = 33) | OLZ + PBO (n = 33) |
|---|---|---|
| Insulin, mIU/L (mean ± SD) | 6.12 ± 2.67 | 7.57 ± 9.96 |
| HOMA2-IR (mean ± SD) | 0.80 ± 0.35 | 0.77 ± 0.37 |
| Triglycerides, mmol/L (mean ± SD) | 0.91 ± 0.36 | 0.95 ± 0.37 |

ALT: alanine aminotransferase,
AST: aspartate aminotransferase,
BMI: body mass index,
HOMA2-IR: homeostatic model assessment 2-insulin resistance,
MIRI: miricorilant,
OLZ: olanzapine;
PBO: placebo,
SD: standard deviation Results Reported adverse events were consistent with those expected for olanzapine. Six participants discontinued the study due to elevated liver enzymes (1 in the OLZ+MIRI group; 5 in OLZ+PBO) and 2 discontinued for personal reasons (1 in OLZ+MIRI; 1 in OLZ+PBO).

As shown in Table 2 (using baseline values from Table 1), body weight increased from baseline by about 3.6% with olanzapine+miricorilant on day 8, as compared to a 4.9% increase with olanzapine+placebo. On day 15, the body weight increase was only 5.4% for olanzapine+miricorilant administration, while the weight gain for olanzapine+placebo was 6.9% of baseline weight. On day 8, insulin increased from baseline by about 92% with olanzapine+miricorilant, as compared to a 121% increase with olanzapine+placebo. On day 15, the insulin increase was only 97% for olanzapine+miricorilant administration, while the insulin increase for olanzapine+placebo was 127%. Insulin resistance (as measured by HOM2-IR) increased from baseline by 150% with placebo (to HOMA2-IR levels about 2.5-fold greater than baseline) while miricorilant administration along with olanzapine reduced the insulin resistance increase to only about 90% (less than 2-fold increase as compared to baseline). (HOMA2-IR values were calculated from fasted glucose and insulin levels using the HOMA (HOMA2 Model) Calculator® application programming interface for SAS (Oxford University 2013, available at the website www.dtu.ox.ac.uk/homacalculator)). On day 8, triglycerides increased from baseline by about 60% with olanzapine+miricorilant, as compared to a 115% increase with olanzapine+placebo. On day 15, the triglyceride increase was only 37% for olanzapine+miricorilant administration, while the triglyceride increase for olanzapine+placebo was 65%. The liver enzyme AST increased by 71% on day 7 with olanzapine+miricorilant, as compared to a 137% increase with olanzapine+placebo. On day 12, the AST increase was 192% for olanzapine+miricorilant administration, while the AST increase for olanzapine+placebo was 338%. The liver enzyme ALT increased by 152% on day 7 with olanzapine+miricorilant, as compared to a 225% increase with olanzapine+placebo. On day 12, the ALT increase was 528% for olanzapine+miricorilant administration, while the ALT increase for olanzapine+placebo was 724%.

TABLE 2

| Parameter | A<br>600 mg<br>miricorilant +<br>olanzapine | B<br>Placebo +<br>olanzapine | p-value | % reduction in<br>OLZ-induced<br>increase* |
|---|---|---|---|---|
| Body weight increase from baseline on Day 8 (kg) | 2.59 | 3.49 | 0.044 | 25% |
| Body weight increase from baseline on Day 15 (kg) | 3.91 | 4.99 | 0.017 | 22% |
| Insulin increase from baseline on Day 8 (mIU/L) | 5.65 | 9.14 | 0.013 | 38% |
| Insulin increase from baseline on Day 15 (mIU/L) | 5.91 | 9.65 | 0.007 | 39% |
| HOMA2-IR increase from baseline on Day 8 | 0.71 | 1.15 | 0.012 | 38% |
| HOMA2-IR increase from baseline on Day 15 | 0.74 | 1.21 | 0.007 | 39% |
| Triglycerides increase from baseline on Day 8 | 0.56 | 1.09 | <0.001 | 49% |
| Triglycerides increase from baseline on Day 15 | 0.34 | 0.62 | 0.057 | 45% |
| AST increase from baseline on Day 7 | 16.61 | 31.17 | 0.25 | 47% |
| AST increase from baseline on Day 12 | 44.83 | 77.07 | 0.009 | 42% |
| ALT increase from baseline on Day 7 | 33.08 | 51.22 | 0.43 | 35% |
| ALT increase from baseline on Day 12 | 115.02 | 165.01 | 0.03 | 30% |

*% reduction in olanzapine-induced increase is calculated as $(1 - (A/B)) \times 100$, where A is the value in column A (600 mg miricorilant + olanzapine) and B is the value in column B (Placebo + olanzapine).

Miricorilant Attenuates Olanzapine-Induced Weight Gain

Participants receiving olanzapine+placebo gained a significant amount of weight over the 14-day duration of the study (5.0 kg by day 15). Co-administration of miricorilant effectively attenuated weight gain (3.9 kg by day 15,). Throughout the study, weight gain was lower in the OLZ+MIRI group compared to OLZ+PBO, resulting in statistically significant differences between the treatment groups of −0.9 kg on day 8 (P=0.044, 95% CI [−1.77, −0.02]) and −1.07 kg on day 15 (P=0.017, 95% CI [−1.94, −0.19]). Data shown are derived from the mixed-effect model with repeated measures (MMRM).

The increase in average body weight was higher in OLZ+PBO vs OLZ+MIRI group at day 8 (3.5 kg vs 2.6 kg, p=0.04, respectively) and day 15 (5.0 kg vs 3.9 kg, p=0.01, respectively). On day 12, the liver enzyme ALT increased by 165.01 IU/L in the OLZ+PBO and 115.02 IU/L in the OLZ+MIRI group; AST increased by 77.07 IU/L in the OLZ+PBO and 44.83 IU/L in the OLZ+MIRI group. Two subjects withdrew consent due to personal reasons. Six subjects discontinued due to elevated liver enzymes (5 were from the OLZ+PBO group, 1 was from the OLZ+MIRI group). (ALT: alanine aminotransferase; AST: aspartate aminotransferase.) Throughout the study, weight gain was lower in the OLZ+MIRI group compared to OLZ+PBO, resulting in statistically significant differences between the treatment groups of −0.9 kg on day 8 (P=0.044, 95% CI [−1.77, −0.02]) and −1.07 kg on day 15 (P=0.017, 95% CI [−1.94, −0.19]). Data shown are derived from the mixed-effect model with repeated measures (MMRM).

Figure 2A:
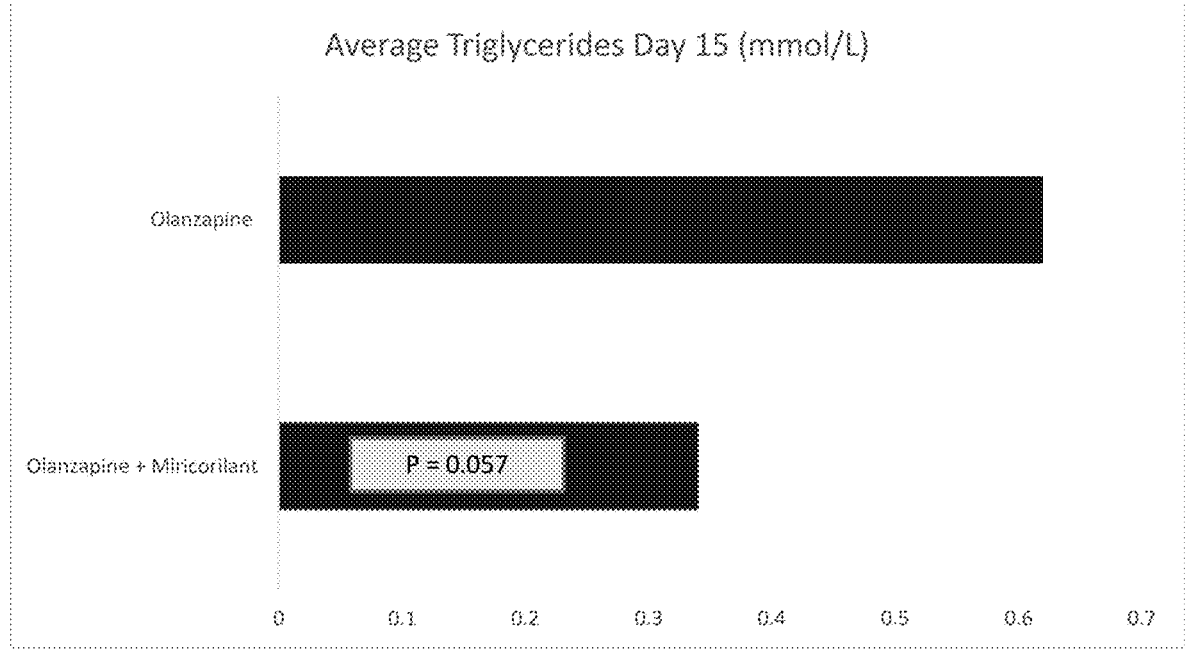
FIG. 2A illustrates the reduction in olanzapine-induced triglyceride increase in healthy subjects.
Figure 2B:
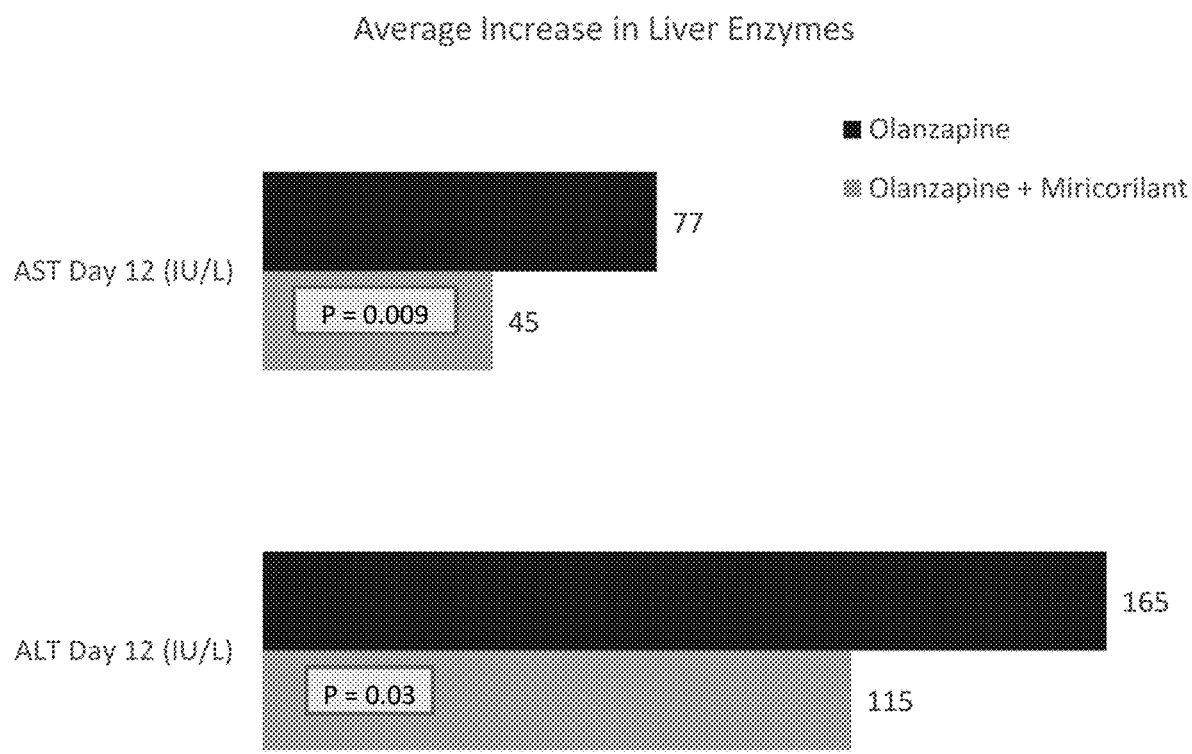
FIG. 2B illustrates the reduction in olanzapine-induced liver enzyme increase in healthy subjects (for liver enzymes aspartate aminotransferase (AST) and alanine aminotransferase (ALT)).

These results are tabulated in Table 2, and are illustrated in FIG. 1 (increase in body weight) and FIGS. 2A and 2B (liver enzymes).

Miricorilant Lowers Olanzapine-Induced Increases in Liver Enzymes

Co-administration of miricorilant with olanzapine resulted in a significantly smaller increase in alanine aminotransferase (ALT) and aspartate aminotransferase (AST) compared to the OLZ+PBO group. On day 12, the difference in AST levels between the OLZ+MIRI and OLZ+PBO groups, based on the MMRM, was −32.24 IU/L (P=0.009), corresponding to an approximately 40% lower increase in AST with miricorilant. Similarly, the difference in ALT levels between the treatment arms, based on the MMRM, was −49.99 IU/L (P=0.03) on day 12. This reflects an about 30% smaller increase in ALT with miricorilant. Notably, 5 of the 6 participants who discontinued the study due to elevated liver enzymes were from the OLZ+PBO group. Co-administration of miricorilant with olanzapine resulted in a smaller increase in AST and ALT. Based on the MMRM model, on day 12, the differences in AST and ALT levels reached statistical significance, −32.24 IU/L (P=0.009, 95% CI [−56.16, −8.33]) and −49.99 IU/L (P=0.03, 95% CI [−95.01, −4.97]), respectively.

Elevated liver enzymes were the only cause of study discontinuation and occurred primarily in the OLZ+PBO group.

These results are tabulated in Table 2 and shown in FIG. 2B (increase in liver enzymes AST and ALT).

Miricorilant Mitigates Olanzapine-Induced Increases in Laboratory Parameters Associated with Metabolic Syndrome Plasma Insulin The difference in plasma insulin increase on day 8 between OLZ+MIRI and OLZ+PBO was −3.49 mIU/L (P=0.013). In the OLZ+MIRI group, insulin levels remained essentially unchanged for the remainder of the study, while they continued to rise in the OLZ+PBO group, resulting in a difference in plasma insulin increase between PBO and OLZ of 3.74 mIU/L (P=0.007) on day 15.

Insulin Resistance—HOMA2-IR

An assessment of insulin resistance using Homeostatic Model Assessment 2 (HOMA2-IR) showed differences of −0.44 (P=0.012) and −0.47 (P=0.007) between the OLZ+MIRI and OLZ+PBO groups on days 8 and 15, respectively (see Table 2).

Triglycerides

Co-administration of miricorilant with olanzapine also attenuated olanzapine-induced increases in triglyceride levels, with differences of −0.53 mmol/L (P<0.001) and −0.28 mmol/L (P=0.057) on days 8 and 15, respectively (see FIG. 2A and Table 2).

Thus, as tabulated in Table 2, shown in the figures, and as discussed above, co-administration of miricorilant with olanzapine resulted in smaller increases in insulin, HOMA2-IR, and triglycerides as compared to placebo on both day 8 and on day 15 of the study.

Thus, miricorilant significantly attenuated the effects of olanzapine on body weight, liver enzymes, plasma insulin, insulin resistance, and triglycerides at a dose that was very well tolerated. Chronic olanzapine treatment is often associated with severe metabolic side effects, which, in turn, increase the risk of type 2 diabetes, cardiovascular disease, and drug noncompliance in schizophrenia patients. The observed attenuation of olanzapine-induced increases in several lab parameters associated with metabolic syndrome when miricorilant is co-administered with olanzapine indicates that miricorilant may be useful in addressing the significant detrimental metabolic effects of antipsychotic medications, and in reducing risk of type 2 diabetes, cardiovascular disease, and drug noncompliance in patients taking antipsychotic medications such as olanzapine.

These results demonstrate that miricorilant can be useful in the amelioration and reduction of significant detrimental metabolic effects associated with antipsychotic medications such as olanzapine. Despite the short duration of treatment, miricorilant was able to significantly attenuate the effects of olanzapine on body weight and liver enzymes. It is believed that higher doses of miricorilant can be attained and would be well-tolerated by human subjects; and longer durations of treatment is also readily provided; thus, further positive benefits of miricorilant treatment are suggested by these results for higher doses, longer duration treatments, and combinations of these.

All patents, patent publications, publications, and patent applications cited in this specification are hereby incorporated by reference herein in their entireties as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A method of treating a subject suffering from antipsychotic-induced weight gain, the method comprising administering to the subject an effective amount of the cyclohexyl pyrimidine glucocorticoid receptor modulator (GRM) miricorilant, (E)-6-(4-Phenylcyclohexyl)-5-(3-trifluoromethylbenzyl)-1H-pyrimidine-2,4-dione, which has the structure:

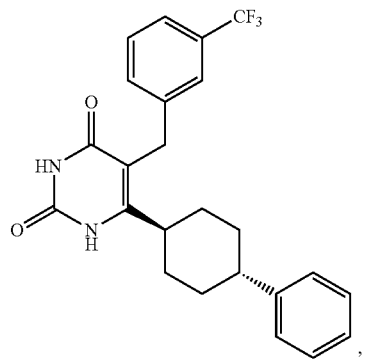 [SMILES: O=c1[nH]c(=O)c(Cc2cccc(C(F)(F)F)c2)c([C@H]2CC[C@H](c3ccccc3)CC2)[nH]1]

while said subject is administered an antipsychotic medication, wherein said treatment is effective to:
reduce the body weight of a subject, as compared to baseline body weight of said subject prior to said administration of said GRM, wherein the subject has previously been administered an antipsychotic medication; or
reduce the weight gain of a subject over time while taking an antipsychotic medication and said GRM, as compared to average weight gain of subjects taking that antipsychotic medication in the absence of the GRM; or
reduce blood levels of triglycerides as compared to triglyceride levels in the blood of said subject prior to said administration of said GRM, wherein the subject has previously been administered an antipsychotic medication; or
reduce blood levels of the liver enzymes alanine aminotransferase (ALT), separate aminotransferase (AST), or both as compared to baseline liver enzyme levels in the blood of said subject prior to said administration of said GRM, wherein the subject has previously been administered an antipsychotic medication; or
reduce plasma insulin level as compared to the baseline plasma insulin level of said subject prior to said administration of said GRM, wherein the subject has previously been administered an antipsychotic medication; or
reduce insulin resistance as compared to baseline insulin resistance of said subject prior to said administration of said GRM, wherein the subject has previously been administered an antipsychotic medication (as measured by HOMA-IR or HOMA2-IR); or
combinations thereof.

2. The method of claim 1, wherein said treatment comprises ameliorating the effects of antipsychotic-induced weight gain in the patient.

3. The method of claim 1, wherein said treatment comprises reducing the effects of antipsychotic-induced weight gain in the patient.

4. The method of claim 1, wherein said treatment comprises reducing the amount of antipsychotic-induced weight gain in the patient.

5. The method of claim 1, wherein said treatment comprises reducing the rate of antipsychotic-induced weight gain in the patient.

6. The method of claim 1, wherein said treatment comprises reversing the antipsychotic-induced weight gain in the patient, whereby said patient loses weight as compared to the patient's weight prior to administration of said GRM.

7. A method of treating a subject at risk of suffering from antipsychotic-induced weight gain, the method comprising administering to the subject an effective amount of the cyclohexyl pyrimidine glucocorticoid receptor modulator (GRM) miricorilant, (E)-6-(4-Phenylcyclohexyl)-5-(3-trifluoromethylbenzyl)-1H-pyrimidine-2,4-dione, which has the structure:

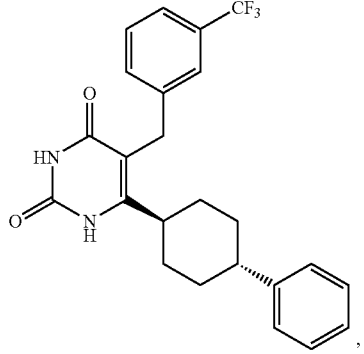 [SMILES: O=c1[nH]c(=O)c(Cc2cccc(C(F)(F)F)c2)c([C@H]2CC[C@H](c3ccccc3)CC2)[nH]1]

while said subject is administered an antipsychotic medication, wherein the subject has not previously been administered an antipsychotic medication, and wherein said treatment is effective to:
reduce the weight gain of a subject over time while taking said antipsychotic medication and said GRM, as compared to average weight gain of subjects administered that antipsychotic medication in the absence of the GRM; or reduce the increase in blood levels of triglycerides as compared to the average increase in triglyceride levels in the blood of subjects administered said antipsychotic medication; or reduce the increase in blood levels of liver enzymes alanine aminotransferase (ALT), or aspartate aminotransferase (AST), or both, as compared to the baseline liver enzyme levels in the blood of subjects prior to administration of said antipsychotic medication; or reduce the increase in plasma insulin level as compared to the average increase in plasma insulin level in subjects administered said antipsychotic medication; or reduce the increase in insulin resistance (as measured by HOMA-IR or HOMA2-IR) as compared to the average increase in insulin resistance of in subjects administered said antipsychotic medication; or combinations thereof.

8. The method of claim 7, wherein said treatment comprises ameliorating the effects of antipsychotic-induced weight gain in the patient.

9. The method of claim 7, wherein said treatment comprises reducing the effects of antipsychotic-induced weight gain in the patient.

10. The method of claim 1, wherein said treatment comprises reducing the amount of antipsychotic-induced weight gain in the patient.

11. The method of claim 1, wherein said treatment comprises reducing the rate of antipsychotic-induced weight gain in the patient.

12. The method of claim 7, wherein said treatment comprises reversing the antipsychotic-induced weight gain in the patient, whereby said patient loses weight as compared to the patient's weight prior to administration of said GRM.

13. The method of claim 1, wherein said GRM administration comprises oral administration of said GRM.

14. The method of claim 7, wherein said GRM administration comprises oral administration of said GRM.

15. The method of claim 1, wherein said treatment comprising concomitant administration of an antipsychotic medication and said GRM is effective to reduce one or more of body weight, weight gain, ALT or AST liver enzyme levels in the blood, plasma insulin, and insulin resistance (HOMA-IR or HOMA2-IR) by about 10% or more as compared to the patient's body weight, weight gain, ALT or AST liver enzyme levels, plasma insulin, or insulin resistance prior to administration of said GRM.

16. The method of claim 7, wherein said treatment comprising concomitant administration of an antipsychotic medication and said GRM is effective to reduce one or more of weight gain, ALT or AST liver enzyme levels in the blood, plasma insulin, and insulin resistance (HOMA-IR or HOMA2-IR) by about 10% or more as compared to average weight gain of subjects administered that antipsychotic medication in the absence of the GRM, or as compared to the patient's ALT or AST liver enzyme levels, plasma insulin, or insulin resistance prior to administration of said GRM.

17. The method of claim 15, wherein said treatment is effective to reduce one or more of body weight, weight gain, ALT or AST liver enzyme levels in the blood, plasma insulin, and insulin resistance (HOMA-IR or HOMA2-IR) by about 20% or more as compared to the patient's body weight, weight gain, ALT or AST liver enzyme levels, plasma insulin, or insulin resistance prior to administration of said GRM.

18. The method of claim 16, wherein said treatment is effective to reduce one or more of weight gain, ALT or AST liver enzyme levels in the blood, plasma insulin, and insulin resistance (HOMA-IR or HOMA2-IR) by about 20% or more as compared to average weight gain of subjects administered that antipsychotic medication in the absence of the GRM, or as compared to the patient's ALT or AST liver enzyme levels, plasma insulin, or insulin resistance prior to administration of said GRM.

\* \* \* \* \*

UNITED STATES PATENT AND TRADEMARK OFFICE
CERTIFICATE OF CORRECTION

PATENT NO. : 11,903,945 B2
APPLICATION NO. : 17/119582
DATED : February 20, 2024
INVENTOR(S) : Ada Lee, Joseph Belanoff and Hazel Hunt Page 1 of 1

It is certified that error appears in the above-identified patent and that said Letters Patent is hereby corrected as shown below:

On the Title Page

In item (57) Abstract: please delete "Methods of Treating Antipsychotic-Induced Weight Gain with Mirocorilant".

In the Claims

Column 26, Line 5, Claim 1: please delete "separate" and insert --aspartate--.

Column 27, Line 29, Claim 10: please delete "claim 1" and insert --claim 7--.

Column 27, Line 32, Claim 11: please delete "claim 1" and insert --claim 7--.

Signed and Sealed this
Ninth Day of April, 2024

Katherine Kelly Vidal
*Director of the United States Patent and Trademark Office*